United States Patent [19]
Isner

[11] Patent Number: 5,830,879
[45] Date of Patent: *Nov. 3, 1998

[54] TREATMENT OF VASCULAR INJURY USING VASCULAR ENDOTHELIAL GROWTH FACTOR

[75] Inventor: Jeffrey M. Isner, Weston, Mass.

[73] Assignee: St. Elizabeth's Medical Center of Boston, Inc., Boston, Mass.

[ * ] Notice: The term of this patent shall not extend beyond the expiration date of Pat. No. 5,652,225.

[21] Appl. No.: 538,301

[22] Filed: Oct. 2, 1995

[51] Int. Cl.$^6$ .......................... A01N 43/04; A61K 31/70; C12N 15/63

[52] U.S. Cl. ........................ 514/44; 435/320.1; 435/69.4; 435/69.6; 435/69.8; 435/172.3; 435/91.2; 536/23.5; 536/23.51

[58] Field of Search ........................... 514/44; 435/320.1, 435/69.4, 69.6, 69.8, 91.2, 172.3; 536/23.5, 23.51

[56] References Cited

U.S. PATENT DOCUMENTS

| | | | |
|---|---|---|---|
| 5,304,121 | 4/1994 | Sahatjian | 604/53 |
| 5,332,671 | 7/1994 | Ferrara et al. | 435/240.1 |

OTHER PUBLICATIONS

Simons & Ware, Nature Medicine, vol. 2, pp. 519–520, May 1996.
Isner et al., Circulation, vol. 91, pp. 2687–2692, Jun. 1, 1995.
Riessen et al., Human Gene Therapy, vol. 4, pp. 749–758, 1993.
Orkin et al., Report and Recommendations of the Panel to Assess the NIH Investment in Research on Gene Therapy, Dec. 7, 1995.
Burke, et al. Biochemical and Biophysical Research Communications. 06 Feb. 1995, vol. 207, No. 1, pp. 348–354.
Isner et al. Lancet. 17 Dec. 1994, vol. 344, pp. 1653–1654.
Feldman et al. Journal of the American College of Cardiology. Sep. 1995, vol. 26, No. 3, pp. 826–835.
Plante et al. Journal of American College of Cardiology. Sep. 1994, vol. 24, No. 3, pp. 820–824.
Feldman et al. Journal of Clinical Investigation. Jun. 1995, vol. 95, pp. 2662–2671.
Asahara et al. Circulation. 01 Nov. 1995, vol. 92, No. 9, pp. II365–II371.
Bauters et al. Circulation. 01 Jun. 1995, vol. 91, No. 11, pp. 2802–2809.
Asahara et al. Circulation. 01 Jun. 1995, vol. 91, No. 11, pp. 2793–2801.
Leclerc et al. Journal of Clinical Investigation. Sep. 1992, vol. 90, pp. 936–944.
Takeshita et al. Circulation. Oct. 1993, vol. 88, No. 4, Part 2, abstract No. 2565, pp. I476–I477.
Flugelman. Thrombosis and Haemostasis. Jul. 1995, vol. 74, No. 1, pp. 406–410.
Feuerstein et al. Expert Opinion on Investigational Drugs. Mar. 1995, vol. 4, No. 3, pp. 237–242.
Wilcox. The American Journal of Cardiology. 18 Oct. 1993, vol. 72, pp. 88E–95E.
Taubman. Thrombosis and Haemostasis. 1993, vol. 70, pp. 180–183.
Wilensky et al. Circulation. 15 Nov. 1995, vol. 92, pp. 2995–3005.
Ip, et al., J. American College of Cardiology, 15:1667–1687, Jun. 1990.
Faxon, et al., Am. Journal of Cariology, 60:5B–9B, 1987.
Bjornsson, et al., Proc. Natl. Acad. Sci. USA, 88:8651–8655, (1991).
Schwarz, et al., J. Vasc. Surg., 5:280–288, (1987).
Keck, et al., Science, 246:1309–1312, 1989.
Ferrera, et al., Biochem Biophys Res Commun., 161:851–855, 1989.
Plouet, et al., Embo J., 3801–3806 (1989).
Connolly, et al., J. Biol. Chem., 264:20017–20024, 1989.
Conn, et al., Proc. Natl. Acad. Sci. USA, 87:1323–1327, 1990.
Shen, et al., Blood, 81:2767–2773, 1993.
Clauss, et al., J. Exp. Med., 172:1535–1545, 1990.
Jorgensen, et al., Lancet, 1:1106–1108, 1989.
Wolinsky, et al., J. Amer. Coll. Cardiol., 15:475–485, 1990.
Dichek, Textbook of Interventional cardiology, vol. 2, 61:989–1005.
Leung, et al., Science, 246:1306–1309, 1989.
Bonnerot, et al., Proc. Natl. Acad. Sci., USA, 84:6795–6799, 1987.
Takeshita, et al., J. Clin. Invest., 93:652–661, 1994.
Weidinger, et al., Circulation, 81:1667–1679, 1990.
Riessen, et al., JACC, vol. 23, No. 5, Apr. 1994:1234–44, "Prospects for Site–Specific Delivery of Pharmacologic and Molecular Therapies".
Feldman, et al., Fundam Clin Pharmacol. (1995) 9, 8–16, "Prevension of restonosis after coronary angioplasty: towards a molecular approach?".

*Primary Examiner*—Brian R. Stanton
*Assistant Examiner*—Jill D. Schmuck
*Attorney, Agent, or Firm*—David G. Conlin; David S. Resnick; Dike, Bronstein, Roberts & Cushman, LLP

[57] ABSTRACT

The present invention provides a method for inducing reendothelialization of the lining of an injured blood vessel comprising contacting the injured portion of the vessel with nucleic acid encoding an endothelial cell mitogen such as vascular endothelial growth factor (VEGF) operably linked to a promoter to result in expression of the mitogen when delivered to the cells at the site of vascular injury. The resulting reendothelialization of the injured blood vessel inhibits smooth muscle cell proliferation and consequently reduces restenosis. The methods of the present invention may be used to treat any blood vessel injury that results in denuding of the endothelial lining of the vessel wall, including, for example, those injuries resulting from balloon angioplasty and deployment of endovascular stents.

5 Claims, 13 Drawing Sheets

TREATMENT OF VASCULAR INJURY USING VASCULAR ENDOTHELIAL GROWTH FACTOR

BACKGROUND OF THE INVENTION

The present invention is directed to a method for enhancing the relining of a blood vessel by use of an endothelial cell (EC) mitogen. This method is particularly useful for reendothelialization of an injured blood vessel.

Atherosclerosis, a common form of arteriosclerosis, results from the development of an intimal lesion and subsequent narrowing of the vessel lumen. As the lesions increase in size, they reduce the diameter of the arteries and impede blood circulation.

Many therapeutical alternatives have been considered for the treatment of atherosclerosis, including surgery and medical treatment. One potential therapy is percutaneous transluminal angioplasty (balloon angioplasty). In balloon angioplasty, a catheter equipped with an inflatable balloon is threaded intravascularly to the site of the atherosclerotic narrowing of the vessel. Inflation of the balloon compresses the plaque enlarging the vessel.

While such angioplasty has gained wider acceptance, it suffers from two major problems, i.e., abrupt closure and restenosis. Abrupt closure refers to the acute occlusion of a vessel immediately after or within the initial hours following a dilation procedure. Abrupt closure occurs in approximately one in twenty cases and frequently results in myocardial infarction and death if blood flow is not restored in a timely manner.

Restenosis refers to the re-narrowing of an artery after an initially successful angioplasty. Restenosis of the blood vessel is thought to be due to injury to the endothelial cells of the blood vessel during angioplasty, or during inflation of the balloon catheter. During healing of the blood vessel after surgery, smooth muscle cells proliferate faster than endothelial cells narrowing the lumen of the blood vessel, and starting the atherosclerotic process anew. In recent years, smooth muscle cell proliferation has been recognized as a major clinical problem limiting the long-term efficacy of percutaneous transluminal coronary angioplasty.

In an effort to prevent restenosis of the treated blood vessel, the search for agents that can reduce or prevent excessive proliferation of smooth muscle cells have been the object of much research. (The occurrence and effects of smooth muscle cell proliferation after these types of surgery have been reviewed, for example, in Ip, et al., (June 1990) *J. Am. College of Cardiology* 15:1667–1687, and Faxon, et al. (1987) *Am. J. of Cardiology* 60: 5B–9B.)

An alternative to prevent problems associated with angioplasty, places endovascular stents in the dilated segments to mechanically block abrupt closure and restenosis. Unfortunately, the use of such stents are limited by direct (subacute thrombosis) or indirect (bleeding, peripheral vascular complications) complications. After stent implantation the patients are threatened with stent thrombosis until the struts of the stent are covered by endothelium. Thus, an aggressive therapy using anticoagulation and/or antiplatelet agents is necessary during this period of time. While these therapies are able to decrease the rate of stent thrombosis, they are the main source of indirect complications.

Thus, the need for a simple and effective means to reduce restenosis is extremely important.

SUMMARY OF THE INVENTION

It has now been discovered that surprisingly nucleic acid (DNA or RNA) capable of expressing an endothelial cell mitogen when delivered to the site of a blood vessel injury, i.e., the denuded endothelial lining of a blood vessel wall, induces reendothelialization of the injured blood vessel and consequently reduces restenosis.

While not wishing to be bound by theory we believe that in contrast to the typical strategies, which have been designed to reduce restenosis by directly inhibiting smooth muscle cell proliferation, our method indirectly inhibits smooth muscle cell proliferation by directly facilitating reendothelialization of the injured vessel.

The present invention provides a method for inducing reendothelialization of the lining of an injured blood vessel comprising contacting the injured portion of the blood vessel with an effective amount of a nucleic acid capable of expressing an endothelial cell mitogen.

The method of the present invention may be used to treat any blood vessel injury that results in denuding of the endothelial lining of the vessel wall, including, for example, those injuries resulting from balloon angioplasty and related devices (e.g., directional atherectomy, rotational atherectomy, laser angioplasty, transluminal extraction, pulse spray thrombolysis) and deployment of an endovascular stent.

The injured portion of the blood vessel may be contacted with the nucleic acid by any means of administration. One preferred means of administration is the use of standard catheter delivery systems known in the art, for example, a double balloon catheter, a porous balloon catheter or a hydrogel polymer coated balloon.

In another embodiment, the blood vessel is contacted with the nucleic acid at the time of vessel injury, for example, at the time of balloon angioplasty or stent deployment. This can be accomplished by incorporating the nucleic acid on the surface of the balloon or stent. The nucleic acid can be incorporated on the balloon surface by means a hydrophilic polymer coating on the balloon surface.

The hydrophilic polymer is selected to allow incorporation of the nucleic acid to be delivered to the site of injury and thereafter released when the hydrophilic polymer contacts the site. Preferably, the hydrophilic polymer is a hydrogel polymer. Other hydrophilic polymers will work, so long as they can retain the nucleic acid, so that, on contact with site, transfer of genetic material occurs.

The injured vessel may also be contacted with the hydrophilic polymer incorporating the nucleic acid by means of an applicator such as a catheter which is coated with the nucleic acid-bearing hydrophilic polymer. Preferably, the applicator can exert some pressure against the arterial cells, to improve contact between the nucleic acid-bearing hydrophilic polymer and the arterial cells. Thus, the use of a balloon catheter is preferred. Preferably, the hydrophilic polymer coats at least a portion of an inflatable balloon of the balloon catheter.

As aforesaid, the nucleic acid may be administered by other means. For example, it may be carried by a microdelivery vehicle such as cationic liposomes or target specific vectors. Such vectors have been described in the art and include those comprising a target moiety and a nucleic acid moiety. Nucleic acid encoding different mitogens may be used separately or simultaneously.

As used herein the term "endothelial cell mitogen" means any protein, polypeptide, mutein or portion that is capable of inducing endothelial cell growth. Such proteins include, for example, vascular endothelial growth factor (VEGF), acidic fibroblast growth factor (aFGF), basic fibroblast growth factor (bFGF), hepatocyte growth factor (j catter factor), and colony stimulating factor (CSF). VEGF is preferred.

The term "effective amount" means a sufficient amount of nucleic acid delivered to the cells at the site of injury to produce an adequate level of the endothelial cell mitogen, i.e., levels capable of inducing endothelial cell growth. Thus, the important aspect is the level of mitogen expressed. Accordingly, one can use multiple transcripts or one can have the gene under the control of a promoter that will result in high levels of expression. In an alternative embodiment, the gene would be under the control of a factor that results in extremely high levels of expression, e.g., tat and the corresponding tar element.

BRIEF DESCRIPTION OF THE DRAWINGS

FIG. 6B shows findings at 4 wks post-transfection.

FIG. 12A shows time course of VEGF gene expression, observed by RT-PCR as early as 3d, with persistent expression through 2 wks, and reduced expression by 3 wks. Arrows indicate position of VEGF band at 258 bp. Arteries transfected with VEGF were examined for the presence of VEGF gene expression by RT-PCR at 3 days (lane 6), 1 wk (lane 7), 2 wks (lane 8), 3 wks (lane 9), 4 wks (lane 10), and 6 wks (lane 11).

Lane 1=positive control (SMC transfected with VEGF); Lane 2=negative control (no RNA); Lane 3=negative control (no tissue); Lane 4=negative control (PCR of LacZ-Tf artery); Lane 5-negative control (PCR of VEGF-Tf artery excluding reverse transcriptase reaction); Lane 12=molecular weight markers, pGEM3zf(−) digested with Hae III.

Figure 12A:
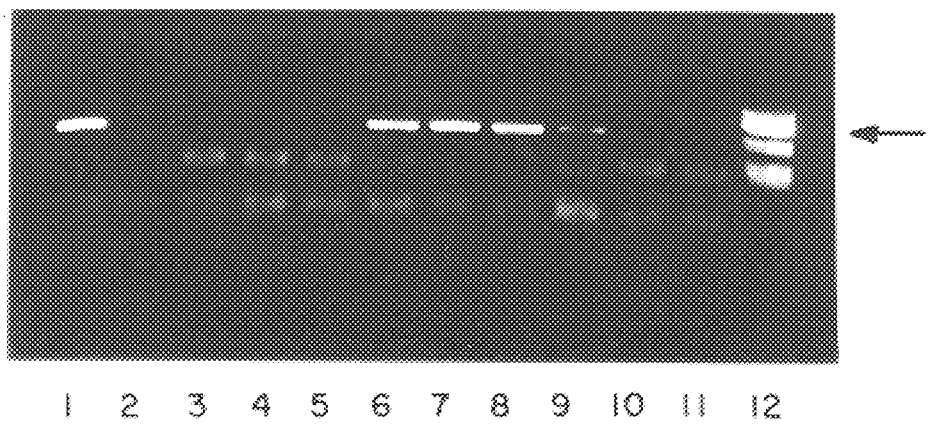
FIGS. 12A and 12B shows VEGF gene expression.
Figure 12B:
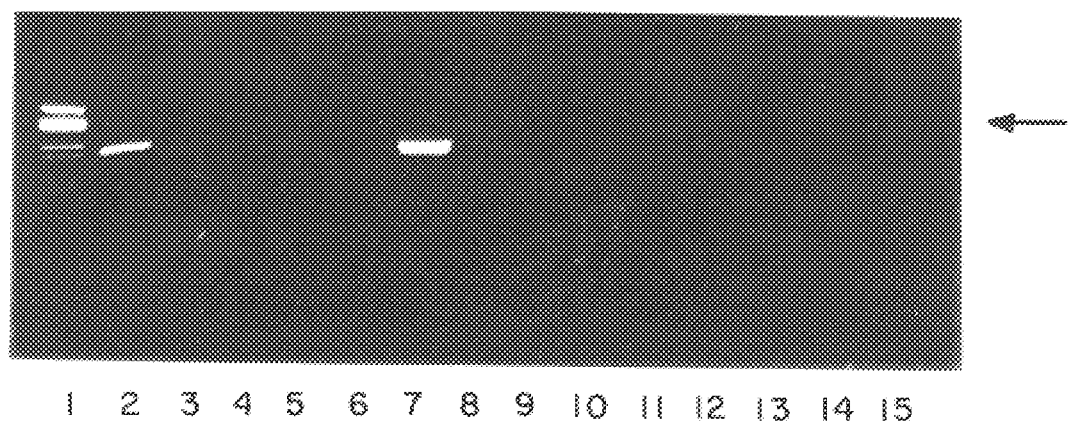

FIG. 12B shows gene expression in organs retrieved from VEGF-transfected rabbit. VEGF mRNA was not observed in any organ (lanes 8–15=heart, lung, liver, spleen, kidney, testis, brain, skeletal muscle from medial thigh) except transfected arterial segment (lane 7). Lane 1=molecular weight markers; Lane 2=positive control (smooth muscle cells transfected with VEGF); Lane 3=negative control (no RNA); Lane 4=negative control (no tissue); Lane 5=negative control (PCR of LacZ-Tf artery); Lane 6=negative control (PCR of VEGF-Tf artery excluding reverse transcriptase reaction).

DETAILED DESCRIPTION OF THE INVENTION

The present invention provides a method for inducing reendothelialization of the lining of an injured blood vessel comprising contacting the injured portion of the vessel with a nucleic acid encoding an endothelial cell mitogen operably linked to a promoter (nucleic acid cassette) to result in expression of the mitogen when delivered to the cells at the site of vascular injury. The resulting reendothelialization of the injured blood vessel inhibits smooth muscle cell proliferation and consequently reduces restenosis. The methods of the present invention may be used to treat any blood vessel injury that results in denuding of the endothelial lining of the vessel wall, including, for example, those injuries resulting from balloon angioplasty and deployment of endovascular stents.

The nucleic acid may be any nucleic acid (DNA or RNA) including genomic DNA, cDNA and mRNA, encoding an endothelial cell mitogen which can be used to express the mitogen, i.e., a protein, polypeptide, mutein or portion that is capable of inducing endothelial cell growth. Such proteins include, for example, vascular endothelial growth factor (VEGF), acidic fibroblast growth factor (aFGF)(Bjornsson, et al., *Proc. Natl. Acad. Sci. USA,* 88:8651–8655, (1991)), basic fibroblast growth factor (bFGF)(Schwarz, et al., *J. Vasc Surg.,* 5:280–288, (1987)), hepatocyte growth factor (j catter factor), and colony stimulating factor (CSF). VEGF is preferred.

VEGF has been shown to be an endothelial cell-specific mitogen (Ferrara, et al., *Biochem Biophys Res Commun.,* 161:851–855, (1989), Keck, et al., *Science,* 246:1309–1312 (1989), and Plouet, et al., *Embo J.,* 3801–3806 (1989)). VEGF was purified independently as a tumor-secreted factor that included vascular permeability by the Miles assay (Keck, et al., supra, and Connolly, et al., *J. Biol. Chem.,* 264:20017–20024 (1989)), and thus has an alternate designation, vascular permeability factor (VPF). Two features distinguish VEGF from other heparin-binding, angiogenic growth factors. First, the $NH_2$ terminus of VEGF is preceded by a typical signal sequence; therefore, unlike bFGF, VEGF can be secreted by intact cells. Second, its high-affinity binding sites, shown to include the tyrosine kinase receptors Flt-1 and Flt-1/KDR are present on endothelial cells. Ferrara, et al., supra, and Conn, et al., *Proc. Natl. Acad. Sci. USA,* 87:1323–1327 (1990). (Interaction of VEGF with lower affinity binding sites has been shown to induce mononuclear phagocyte chemotaxis). Shen, et al., *Blood,* 81:2767–2773 (1993) and Clauss, et al., *J. Exp. Med.,* 172:1535–1545 (1990). DNA capable of encoding VEGF is disclosed in U.S. Pat. No. 5,332,671, the disclosure of which is herein incorporated by reference.

The nucleotide sequence of numerous peptides and proteins, including endothelial cell mitogens, are readily available through a number of computer data bases, for example, GenBank, EMBL and Swiss-Prot. Using this information, a DNA or RNA segment encoding the desired may be chemically synthesized or, alternatively, such a DNA or RNA segment may be obtained using routine procedures in the art, e.g, PCR amplification.

To simplify the manipulation and handling of the nucleic acid encoding the mitogen, the nucleic acid is preferably inserted into a cassette where it is operably linked to a promoter. The promoter must be capable of driving expression of the mitogen in the desired target host cell. The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., *Hum Gene Ther* 4:151 (1993)) and MMT promoters may also be used. Certain proteins can expressed using their native promoter. Other elements that can enhance expression can also be included such as an enhancer or a system that results in high levels of expression such as a tat gene and tar element. This cassette can then be inserted into a vector, e.g., a plasmid vector such as pUC118, pBR322, or other known plasmid vectors, that includes, for example, an *E. coli* origin of replication. See, Sambrook, et al., *Molecular Cloning: A Laboratory Manual,* Cold Spring Harbor Laboratory press, (1989). The plasmid vector may also include a selectable marker such as the β-lactamase gene for ampicillin resistance, provided that the marker polypeptide does not adversely effect the metabolism of the organism being treated. The cassette can also be bound to a nucleic acid binding moiety in a synthetic delivery system, such as the system disclosed in WO 95/122618.

If desired, the DNA may also be used with a microdelivery vehicle such as cationic liposomes and adenoviral vectors. For a review of the procedures for liposome preparation, targeting and delivery of contents, see Mannino and Gould-Fogerite, *Bio Techniques,* 6:682 (1988). See also, Feigner and Holm, *Bethesda Res. Lab. Focus,* 11 (2):21 (1989) and Maurer, R. A., *Bethesda Res. Lab. Focus,* 11(2):25 (1989).

Replication-defective recombinant adenoviral vectors, can be produced in accordance with known techniques. See, Quantin, et al., *Proc. Natl. Acad. Sci. USA,* 89:2581–2584 (1992); Stratford-Perricadet, et al., *J. Clin. Invest.,* 90:626–630 (1992); and Rosenfeld, et al., *Cell,* 68:143–155 (1992).

The injured portion of the blood vessel is contacted with the DNA encoding an endothelial cell mitogen by any means familiar to the skilled artisan, including, for example, double-balloon catheters, porous-balloon catheters and hydrophilic coated balloon catheters. See, Jorgensen, et al., *Lancet* 1:1106–1108, (1989); Wolinsky, et al., *J. Am. Coll. Cardiol.,* 15:475–485 (1990); March, et al., *Cardio Intervention,* 2:11–26 (1992)); WO93/00051 and WO93/00052; U.S. Pat. No. 5,304,121. See also Dichek, *Textbook of Interventional Cardiology,* Vol. 2, 61:989–1005.

A hydrophilic coated balloon catheter is preferred in certain situations. A hydrophilic coated balloon catheter has a hydrophilic polymer on the outer surface of the balloon which permits the contact between the hydrophilic polymer bearing the nucleic acid to be transferred and the cells of the injured portion of the blood vessel to be made with some pressure, thus facilitating the transfer of the nucleic acid to the cells. However, other supports for the hydrophilic polymer are also useful, such as catheters or solid rods having a surface of hydrophilic polymer. Preferably, the catheters or rods or other substrates which are flexible, to facilitate threading through the arteries to reach the point of intended application.

Preferably, the hydrophilic polymer is a hydrogel polymer, a cross-linked polymer material formed from the combination of a colloid and water. Cross-linking reduces solubility and produces a jelly-like polymer that is characterized by the ability to swell and absorb liquid, e.g., that containing the DNA. Suitable hydrogel polymers include, for example, those selected from the group consisting of polycarboxylic acids, cellulosic polymers, gelatin, polyvinylpyrrolidone, maleic anhydride polymers, polyamides, polyvinyl alcohols, and polyethylene oxides. Preferred hydrogels are polyacrylic acid polymers available as HYDROPLUS (Mansfield Boston Scientific Corp., Watertown, Mass.) and described in U.S. Pat. No. 5,091,205.

When a hydrophilic arterial balloon is used, it is not necessary to protect the balloon prior to inflation, since relatively little of the nucleic acid is lost in transit to the treatment site until the balloon is inflated and the hydrophilic polymer bearing the nucleic acid is pressed against the injured site. When hydrophilic polymer-surfaced catheters or rods are used as the vehicle or substrate, the surface can protected, e.g. by a sheath, until the point of intended application is reached, and then the protection removed to permit the hydrophilic polymer bearing the nucleic acid to contact the injured site.

The nucleic acid in aqueous solution is incorporated into the hydrophilic polymer to form a nucleic acid-hydrophilic polymer composition. The nucleic acid is incorporated without complexing or chemical reaction with the hydrophilic polymer, and is preferably relatively freely released therefrom when placed in contact with the cells at the site of injury. The resulting structure comprises a support, e.g. the balloon of the balloon catheter, on which is mounted the hydrogel, in or on which is incorporated the desired DNA and its associated vehicle, e.g., phage or plasmid vector. The hydrophilic polymer is preferably adhered to the support, so that after application of the DNA to the target cells, the hydrophilic polymer is removed with the support.

Preferably, the nucleic acid-hydrophilic composition contacts the arterial cell by means of a catheter. The catheter is preferably a balloon catheter constructed for insertion in a blood vessel and has a catheter shaft and an expandable dilation balloon mounted on the catheter shaft. At least a portion of the exterior surface of the expandable portion is defined by a coating of a tenaciously adhered hydrophilic polymer. Incorporated in the hydrophilic polymer is an aqueous solution of the DNA to be delivered to the cells of the injured portion of the blood vessel.

In general, when dry, the hydrophilic polymer (preferably hydrogel) coating is preferably on the order of about 1 to 10 microns thick, with a 2 to 5 micron coating typical. Very thin hydrogel coatings, e.g., of about 0.2–0.3 microns (dry) and much thicker hydrogel coatings, e.g., more than 10 microns (dry), are also possible. Typically, hydrogel coating thickness may swell by about a factor of 2 to 10 or more when the hydrogel coating is hydrated.

Procedures for preparing and using a balloon with a hydrogel coating are set forth in U.S. Pat. No. 5,304,121, the disclosure of which is incorporated herein by reference.

Figure 1:
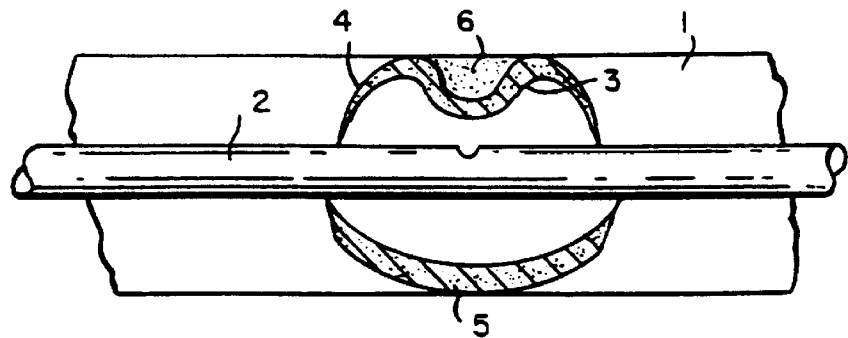
FIG. 1 illustrates a diagrammatical cross section of a balloon catheter delivering nucleic acid encoding an endothelial cell mitogen to an occlusion during balloon angioplasty.

A representative catheter is set forth in FIG. 1. Referring to FIG. 1, 1 is the wall of the blood vessel. The figure shows the catheter body 2 held in place by the inflation of a balloon 3 inflated at the site of occlusion 6. The balloon comprises a hydrogel coating 4 incorporating DNA 5.

When a hydrophilic coated balloon is used to practice the method of the present invention, the nucleic acid, e.g., DNA, is applied ex vivo to the hydrophilic polymer coating of the balloon. To facilitate application, the balloon may be inflated. If necessary, the polymer may be dried with warm air and the DNA application repeated. The amount of DNA to be applied to the arterial surface depends on the ability of the DNA to be expressed in the arterial cells. Generally, the amount of naked DNA applied to the balloon catheter is between about 0.1 and 100 $\mu g/mm^2$, more preferably between about 0.5 and about 20 $\mu g/mm^2$, most preferably between about 1.5 and about 8 $\mu g/mm^2$. Preferably, between 0.5 mg and 5 mg of DNA are applied to the hydrogel coating of a balloon catheter having an inflated lateral area of about 630 $mm^2$ (e.g., a balloon catheter having an inflated diameter of about 5 mm and a length of about 40 mm), providing a surface having about 0.8 to about 8 $\mu g/mm^2$ of DNA when the balloon is inflated and contacts the interior of the artery. More preferably, between 1 mg and 3 mg of DNA are applied to the polymer, providing a DNA loading of about 1.6 to about 4.8 $\mu g/mm^2$.

The catheter is inserted using standard percutaneous application techniques and directed to the desired location, e.g., an occlusion or stent. For example, in the treatment of atherosclerosis, the balloon is directed towards an arterial occlusion. Once the balloon, for example, a hydrogel coated balloon, has reached its desired location, it is inflated such that the hydrogel coating of the balloon contacts the occlusion causing release of the DNA directly into the arterial tissue. The introduction of the DNA into the plaque and surrounding tissue occurs simultaneously with the opening of the occlusion of the dilation balloon. Thus, as cracking of the plaque and stimulation of smooth muscle cells beneath the plaque and along healthy tissue of the vessel wall are caused by dilatation, the DNA encoding the endothelial cell mitogen is simultaneously applied to the denuded endothelial lining of the blood vessel where it is expressed facilitating re-endothelialization, thus reducing restenosis. Preferred periods of balloon inflation range from 30 seconds to 30 minutes, more preferably 1 minute to 5 minutes.

Once transferred, the DNA is expressed by the cells at the site of injury for a period of time sufficient for reendothelialization. Because the vectors containing the DNA are not normally incorporated into the genome of the cells, expression of the protein of interest takes place for only a limited time. Typically, the endothelial cell mitogen is only expressed in therapeutic levels for about two days to several weeks, preferably for about 1–2 weeks. Reapplication of the DNA can be utilized to provide additional periods of expression of the therapeutic polypeptide.

The vehicle, be it arterial balloon, catheter, flexible rod or other shaped vehicle, can be furnished with means to assist in accurate placement within the intended body cavity. For example, it can be furnished with a radioactive element, or made radio-opaque, furnished with means permitting easy location using ultrasound, etc.

The methods of the present invention may be used to treat other blood vessel injuries that result in denuding of the endothelial lining of the vessel wall. For example, primary angioplasty is becoming widely used for the treatment of acute myocardial infarction. Acceleration of reendothelialization using the method of the present invention can stabilize an unstable plaque and prevent re-occlusion.

In addition, endovascular stents are becoming widely used as an adjunct to balloon angioplasty. Stents are useful for rescuing a sub-optimal primary result as well as for diminishing restenosis. To date, however, the liability of the endovascular prosthesis has been its susceptibility to thrombotic occlusion in approximately 3% of patients with arteries 3.3 mm or larger. If patients undergo stent deployment in arteries smaller than this the incidence of sub-acute thrombosis is even higher. Sub-acute thrombosis is currently prevented only by the aggressive use of anticoagulation. The combination of vascular intervention and intense anticoagulation creates significant risks with regard to peripheral vascular trauma at the time of the stent/angioplasty procedure. Reendothelialization of the portion of the vessel injured by the stent deployment can eliminate these liabilities, thereby attenuating the thrombogenicity of the stented site and also reducing smooth muscle cell proliferation, responsible for stenosis in 10 to 15% of patients who undergo stent therapy. The elimination of an aggressive anticoagulation regiment constitutes a significant improvement in utilizing stent technology. Multiple stents have a higher rate of subacute thrombosis and restenosis which can be reduced by use of the methods of the present invention. Furthermore, by utilizing the method of the present invention stent deployment can now be applied to patients with arteries smaller than 3.0 mm in diameter.

All documents mentioned herein are incorporated by reference herein in their entirety.

The present invention is further illustrated by the following examples. These examples are provided to aid in the understanding of the invention and are not construed as a limitation thereof. Throughout the examples the following abbreviations are used: Ach, acetylcholine chloride; EC, endothelial cell; LacZ, gene encoding nuclear-targeted β-galactosidase; nTf, non-transfected; rET, re-endothelialization; and Tf, transfected.

EXAMPLE 1

Re-Endothelialization of a Balloon Injured Arterial Segment

Animals

Figure 2:
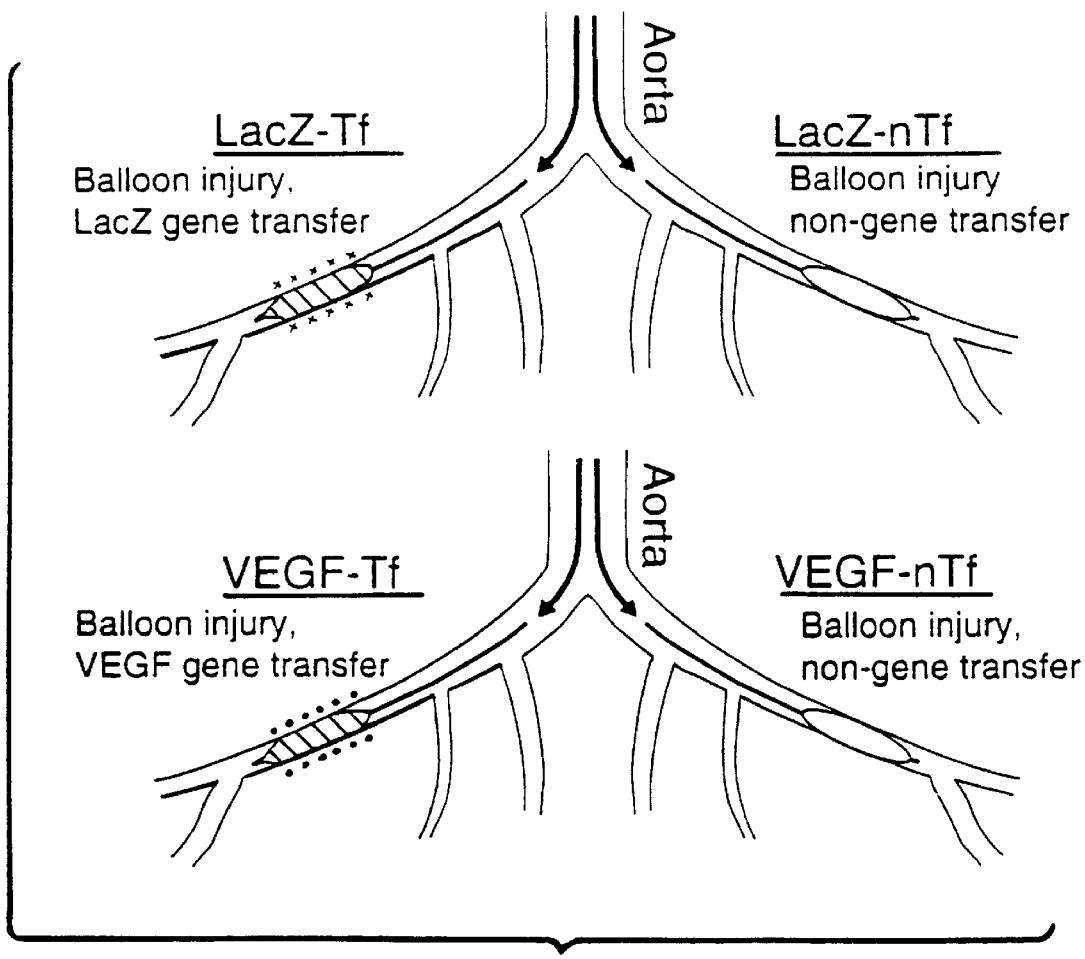
FIG. 2 is a diagram illustrating the experimental protocol of Example 1. LacZ or phVEGF$_{165}$ plasmid DNA (10 $\mu$g/$\mu$L, total=400 $\mu$g) was applied to the external hydrogel polymer coating a 2.0 mm diameter, 2.0 cm long, hydrogel-coated balloon catheter (Slider with Hydroplus, Boston Scientific, Watertown, Mass.). The catheter was advanced via a 5 Fr. teflon protective sheath (Boston Scientific), designed to minimize contact between blood and the balloon, into one femoral artery. Balloon inflation was then performed 3 times for 1 min each at 4 atm. For each rabbit, after completion of transfection of one femoral artery (with phVEGF$_{165}$ or pGSVLacZ), the contralateral femoral artery underwent balloon injury (but no transfection) using a new catheter.
Figure 3:
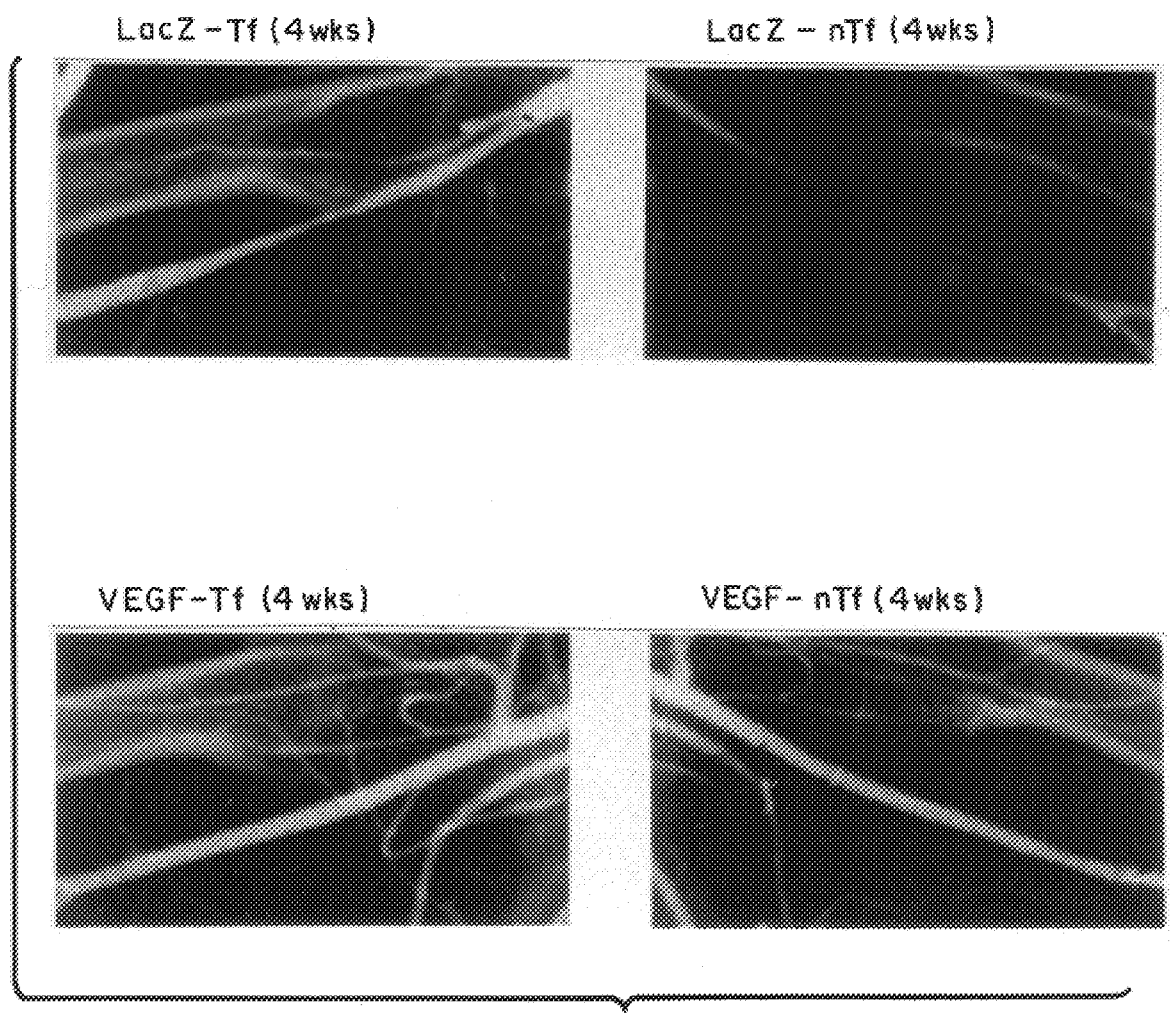
FIG. 3 shows representative angiograms 4 wks after balloon-injury and/or transfection.

Male New Zealand White rabbits (3.5–4.0 kg)(Pine Acre Rabbitry, Norton, Mass.) were used for all experiments, according to protocols approved by St. Elizabeth's Institutional Animal Care and Use Committee. In 32 rabbits, one femoral artery underwent simultaneous balloon injury and transfection with $phVEGF_{165}$ (VEGF-Tf), while the contralateral femoral artery underwent identical balloon injury but no gene transfer (VEGF-nTf), while the contralateral femoral artery underwent identical balloon injury but no gene transfer (VEGF-nTf)(FIG. 2). Another group of 32 rabbits underwent simultaneous balloon injury and transfection of one femoral artery with β-Gal (LacZ-Tf), while the contralateral femoral artery underwent identical angioplasty balloon injury but no gene transfer (LacZ-nTf). The angiographic and histologic consequences of VEGF vs LacZ gene transfer were systematically studied in these 64 animals at the following time points: 3 days (n=4 each group), 5 days (n=4 each), 1 wk (n=8 each), 2 wk (n=8 each) and 4 wk (n=8 each). An additional 18 rabbits were transfected with $phVEGF_{165}$ and used, along with 3 normal non-instrumented rabbits, to determine the time course of VEGF gene expression at 0 days (pre-angioplasty), 3 days, 5 days, 1 wk, 2 wks, and 4 wks (3 animals at each time point). Finally four rabbits were transfected with β-Gal and sacrificed 5 days later to assess the transfection efficiency in this model.

Plasmid DNA

The mammalian expression vector employed in these experiments contains a cytomegalovirus promoter and the cDNA for recombinant human $VEGF_{165}$; the latter was initially isolated from cDNA libraries prepared from HL60 leukemia cells (Leung, et al., *Science*, 246:1306–1309 (1989)). Expression of this plasmid in rabbit vascular smooth muscle cells was previously documents in vitro by immunoabsorbent assay for VEGF protein at 3 days post-transfection (Isner, et al., *Circulation*, 91:2687–2692 (1995) ). The biological activity of $VEGF_{165}$ secreted from cells transfected with this construct ($phVEGF_{165}$) was previously confirmed by the finding that media conditioned by transfected human 293 cells promoted the proliferation of capillary cells (Leung, et al., supra) in vitro; and angiographic and histochemical evidence of angiogenesis following catheter administration of the vector in vivo (Isner, et al., supra).

The plasmid pGSVLacZ (courtesy of Dr. Claire Bonnerot) containing a nuclear targeted β-galactosidase sequence coupled to the simian virus 40 early promoter (Bonnerot, et al., *Proc. Natl. Acad. Sci. USA*, 84:6795–6799 (1987)) was used for all control transfections as previously described (Takeshita, et al., *J Clin Invest.*, 93:652–661 (1994)).

Percutaneous arterial gene and balloon angioplasty in vivo

Each rabbit was anesthetized with ketamine (10 mg/kg) and acepromazine (0.2 mg/kg) following premedication with xylazine (2 mg/kg). Supplemental anesthetic doses were not required. Spontaneous ventilation was maintained throughout the intervention. Access to the right common carotid artery was obtained via a small midline incision in the neck. In each rabbit, a 2.0 mm diameter, 2.0 cm long, hydrogel-coated balloon catheter (Slider with Hydroplus, Boston Scientific, Watertown, Mass.) was used to perform balloon angioplasty and arterial gene transfer (Riessen, et al., *Hum Gene Ther.*, 4:749–758 (1993)). The angioplasty balloon was prepared ex vivo by first advancing the deflated balloon through a 5 Fr. teflon protective sheath (Boston Scientific), designed to minimize contact between blood and the balloon upon introduction of the catheter into the carotid artery. To apply plasmid DNA to the exterior hydrogel polymer coating the angioplasty balloon, the balloon was inflated to 3 atm. pressure. A conventional pipette was then used to apply 400 μg of $phVEGF_{165}$ to the 20 μm-thick later of hydrogel polymer coating the external surface of the inflated balloon. The plasmid DNA was applied at a concentration of 10 μg/μL. Once dried, the applied plasmid solution imparts a grossly visible white glaze to the balloon surface. The balloon was next deflated, withdrawn back into the protective sheath, and reinflated to 3 atm within the sheath to again minimize blood flow across the balloon surface. The sheath and angioplasty catheter was then introduced via the right common carotid artery, and advanced to the lower abdominal aorta using a 0.014 in. guidewire (Hi-Torque Floppy II, Advanced Cardiovascular Systems, Temecula, Calif.) under fluoroscopic guidance. The balloon catheter was then deflated and advanced into one femoral artery where it was positioned using angiographic landmarks. Balloon inflation was then performed 3 times for 1 min each at 4 atm. Following the final deflation, the balloon and sheath were withdrawn. An identical protocol was employed to transfect the femoral artery of control animals with the plasmid pGSVLac containing a nuclear targeted β-galactosidase sequence.

For each rabbit, after completion of transfection of one femoral artery (with $phVEGF_{165}$ or pGSVLacZ), the contralateral femoral artery underwent balloon injury (but no transfection) using a new 2.0 mm diameter, 2.0 cm long hydrogel-coated angioplasty balloon. Balloon injury, with or without gene transfer, was performed by one person who was blind to the treatment. Following completion of the entire procedure, nitroglycerin (0.25 mg, SoloPak Laboratories, Franklin Park, Ill.) and heparin sodium (200 USP units, Elkins-sinn, Cherry Hill) N.J. were administered intraarterially to prevent acute occlusion of the balloon-injured sites.

In vivo vasometer reactivity

Vasometer reactivity of the arterial segment subjected to balloon angioplasty and arterial gene transfer was evaluated on the day of sacrifice. A 3 Fr., end-hole infusion catheter (Tracker-18™, Target Therapeutics, San Jose, Calif.) was inserted into the left carotid artery and advanced to the origin of transfected iliac artery using a 0.018 in. guidewire (Hi-Torque Floppy II) under fluoroscopic guidance. This catheter was used both for infusion of vasoactive drugs and selective angiography of the femoral artery. Angiography was performed immediately after drug administration using 1 ml of non-ionic contrast media (Isovue-370, Squibb Diagnostics, New Brunswick, N.J.). Serial angiographic images were recorded on 105-mm spot film at a rate of 2 films per sec. for 4 sec.

To assess endothelium-dependent vasomotor reactivity, acetylcholine chloride (Ach) and serotonin creatine sulfate (5-HT) were delivered from a constant infusion pump (1 ml/min) via the 3 Fr. catheter at doses of 0.15, 1.5, and 15 μg/kg/min, each for 2 min. Five min was allowed to elapse between each dose of agent to re-establish basal blood flow conditions. After administration of Ach and 5-HT respectively were completed, a 2-min intra-arterial infusion of sodium nitroprusside (Np)(1.5 μg/kg/min) was administered to assess endothelium-independent vasomotorreactvity. Finally, an identical protocol was employed to evaluate the contralateral injured but non-transfected femoral artery.

Quantitative angiography

The angiographic luminal diameter of the femoral artery prior to and after drug infusion was determined using an automated edge-detection system (LeFree, et al., *Proc SPIE*, 626:334–341 (1986) and Mancini, et al., *Circulation*, 75:452–460 (1987)). Each balloon-injured site was defined and the boundary lines were draw according to the pilot angiogram of angioplasty balloon injury. The angiogram selected for analysis was scanned with a high resolution video camera; the signal produced by the video camera was digitized and displayed on a video monito. Center-lines were traced manually for a 20 mm-long segment defined by the boundary lines drawn previously. Contours were detected automatically on the basis of the weighted sum of first and second derivative functions applied to the digitized brightness information. The average angiographic luminal diameter and the minimum luminal diameter were then determined for the defined 20 mm-long segment of each transfected as well as non-transfected balloon-injured artery.

Drugs

Ach, 5-HT and Np were obtained from Sigma Chemical Co., St. Louis, Mo. Fresh stock solutions of each were prepared immediately before each experiment.

Animal sacrifice

Thirty minutes prior to sacrifice, all rabbits received an intravenous injection of 6 ml 0.5% Evans blue dye (Sigma) (3) delivered via the ear vein to identify the remaining non-endothelialized area. Under ketamine (10 mg/kg) and acepromazine (0.2 mg/kg) anesthesia, a cannula was inserted into the lower abdominal aorta and used to perfuse a total of 100 ml of 0.9% saline solution with 10 units/ml heparin in situ, followed by 100 ml of 100% methanol. The baseline angiogram recorded prior to balloon injury and the pilot radiographic recording of the angioplasty balloon were used to identify the arterial segment to be harvested. The initially injured 2-cm long segment of femoral artery was then dissected free and incised longitudinally. The harvested arterial segment was pinned to a cork board, further fixed in 100% methanol, and photographed using a dissecting microscope (STEMI SR, Zeiss, Germany) in preparation for planimetric analysis of rET (see below). Tissues were further fixed by immersion in 100% methanol, embedded on longitudinal edge in paraffin, and cut in 5-μm sections onto slides coated with 3-aminopropyl-triethoxy-silane.

Planimetric analysis of re-endotheliazation

Planimetric analysis was performed using the photograph of the harvested arterial segment taken through the dissecting microscope. The area of the intimal surface which was stained blue following application of Evans blue dye was interpreted to identify the portion of the arterial segment which remained endothelium-deficient; these macroscopic analyses were confirmed by immunostaining of light microscopic sections using an endothelial cell-specific marker (vide infra). A computerized sketching program (MacMeasure version 1.9; NIMH, Bethesda, Md.) interfaced with a digitizing board (Summagraphics, Fairfield, Conn.) was used by one person blinded to the treatment protocol to outline the Evans blue positive and negative areas respectively. Specifically, the extent of endothelialized area was calculated as a percent of the total intimal area encompassed within the 2-cm length of artery.

Evaluation of intimal hyperplasia

Longitudinal histologic sections obtained from the 20 mm-length of injured artery and stained with an elastic tissue trichrome stain were projected onto the digitizing board, and the area of the intima and media respectively were measured using the computerized sketching program described above by a technician blinded to treatment regiment.

The thickness of the native media of the artery wall is variable reflecting in part the dimensions (diameter) of the individual rabbit femoral artery. Accordingly, thickness of the media was used to index the extent of neointimal thickening, and is thus stated as the ratio of intima to media area (I/M).

Evaluation of proliferative activity in injured artery

Proliferative activity in the injured arterial segment harvested at the time of sacrifice was evaluated by immunostaining analysis for proliferating cell nuclear antigen (PCNA) as previously described (Pickering, et al., *J Clin Invest.*, 91:1469–1480 (1993)). Endogenous peroxide activity was blocked with 3.0% hydrogen peroxide in PBS. Nonspecific protein binding was blocked with 10% normal horse serum. Sections were incubated overnight at 4° C. with a mouse monoclonal antibody against PCNA (clone PC10, Signet, Dedham, Mass.) at a dilution of 1:40 in 1% BSA/PBS. Negative controls were incubated with MOPC-21, a purified non-specific mouse monoclonal antibody (Sigma). Bound primary antibody was detected using an avidin-biotin-immunoperoxidase method (Elite Avidin-Biotin Detection System, Signet). Sections were lightly counterstained with Bandeiraea simplicifolia I (BSI) lectin 5 μg/ml, Vector Laboratories, Burlingame, Calif.)(25). For lectin staining, sections pretreated with 0.3% hydrogen peroxidase were incubated with 5 μg/ml of biotinylated lectin (Vector) overnight at 4° C. After washing, slides were incubated with peroxidase conjugated streptavidin (BioGenex Laboratories, San Ramon, Calif.) for 1 hour; 3-amino-9-ethylcarbazole (AEC, Signet) was then applied as a substrate for the enzyme, resulting in a brown reaction product.

The extent of proliferative activity for each longitudinal section was measured by one person blinded to the treatment regimen as the number of positive cells in the intima per length of the 20 mm-long longitudinal section, i.e. cells/mm. PCNA staining of the rabbit ileum served as the positive control for this study.

Analysis of gene expression

Expression of $phVEGF_{165}$ was evaluated using reverse transcription-polymerase chain reaction (RT-PCR). Total cellular RNA was isolated from transfected arterial segments using TRI REAGENT (Molecular Research Center, Cincinnati, Ohio). Extracted RNA was treated with DNase (0.5 μl, 10 U/μl, RNase-free, Message Clean kit, GenHunter, Boston, Mass.) at 37° C. for 30 min to eliminate DNA contamination. The yield of extracted RNA was determined spectrophotometrically by ultraviolet absorbance at 260 nm. To determine that RNA was not degraded and that ribosomal bands were intact, 1 mg of each RNA sample was heat-denatured and electrophoresed through a 1% non-denaturing mini-agarose gel. We used 0.5 μg of each RNA sample to make cDNA in a reaction volume of 20 μl containing 0.5 mM each of deoxynucleotide triphosphate (Pharmacia, Psicataway, N.J.), 10 mM dithiothreitol, 10 units of RNasin (Promega, Madison, Wis., 50 mM Tris-HCl [pH 8.3], 75 mM KCl, 3 mM $MgCl_2$, 1 mg random hexanucleotide primers (Promega), and 200 units of M-MLV reverse transcriptase (GIBCO BRL, Gaithersburg, Md.). For greater accuracy and reproducibility, master mixes for a number of reactions were made up and aliquoted to tubes containing RNA. Reactions were incubated at 42° C. for 1 hr, then at 95° C. for 5 min to terminate the reaction. Twenty ml of diethyl pyrocarbonate (DEPC) water was then added and 5 ml of the diluted reaction (⅛th) was used in the PCR analysis. The optimized reaction in a total volume of 20 μl contained 0.2 mM of each deoxynucleotide triphosphate, 3 mM $MgCl_2$, 2 ml PCR II buffer (Perkin-Elmer, Norwalk, Conn.; final concentrations, 50 mM KCl, 10 mM Tris-HCl), 5 ng/ml (13.77 pmoles) of each primer, and 0.5 units of AmpliTaq DNA polymerase (Perkin-Elmer). The PCR was performed on a 9600 PCR system (Perkin-Elmer) using microamp 0.2 ml thin-walled tubes. Amplification was performed for 35–45 cycles of 94° C. for 20 sec, 55° C. for 20 sec, and 72° C. for 20 sec, ending with 5 min at 72° C. To test for false positives, controls were includes with no RNA and no transverse transcriptase. A pair of oligonucleotide primers (22 mers) was designed to amplify a 258 bp sequence from the mRNA of human VEGF. To ensure specificity and avoid amplification of endogenous rabbit VEGF, each primer was selected from a region which is not conserved among different species. Sequences of primers used were: 5'-GAGGGCAGAATCATCACGAAGT-3' (SEQ ID NO:1)(sense); and 5'-TCCTATGTGCTGGCCTTGGTGA-3' (SEQ ID NO:2) (antisense). Preliminary experiments showed that cultured rabbit smooth muscle cells hybridized with this primer only when transfected with a plasmid containing the cDNA for human VEGF. Cultures of normal (non-transfected) or β-galactosidase-transfected rabbit smooth muscle cells showed no hybridization. RT-PCR products were analyzed by 2% agarose gel electrophoresis. DNA bands were visualized under UV illumination after staining with ethidium bromide.

To assess the efficiency of in vivo arterial gene transfer in this mode, LacZ-Tf arteries were harvested at day 5, and β-galactosidase activity was determined by incubation with 5-bromo-4-chrolo-3-indolylβ-D-galactoside chromogen (X-Gal, Sigma) as previously described (Riessen, et al., supra). Following staining with X-Gal solution, tissues were paraffin-embedded, sectioned, and counterstained with nuclear fast red. Nuclear localized β-galactosidase expression of the plasmid pGSVLacZ could not result from endogenous β-galactosidase activity; accordingly, histochemical identification of β-galactosidase within the cell nucleus was interpreted as evidence for successful gene transfer and gene expression, Cytoplasmic or other staining was considered non-specific for the purpose of the present study.

Statistical analysis

All results are expressed as mean ± standard error (m±SE), Statistical significance was evaluated using unpaired Student's t test for comparisons between two means or contingency table analysis for comparisons of frequency. A value of $p<0.05$ was interpreted to denote statistical significance.

RESULTS

Re-endothelialization

Figure 4A:
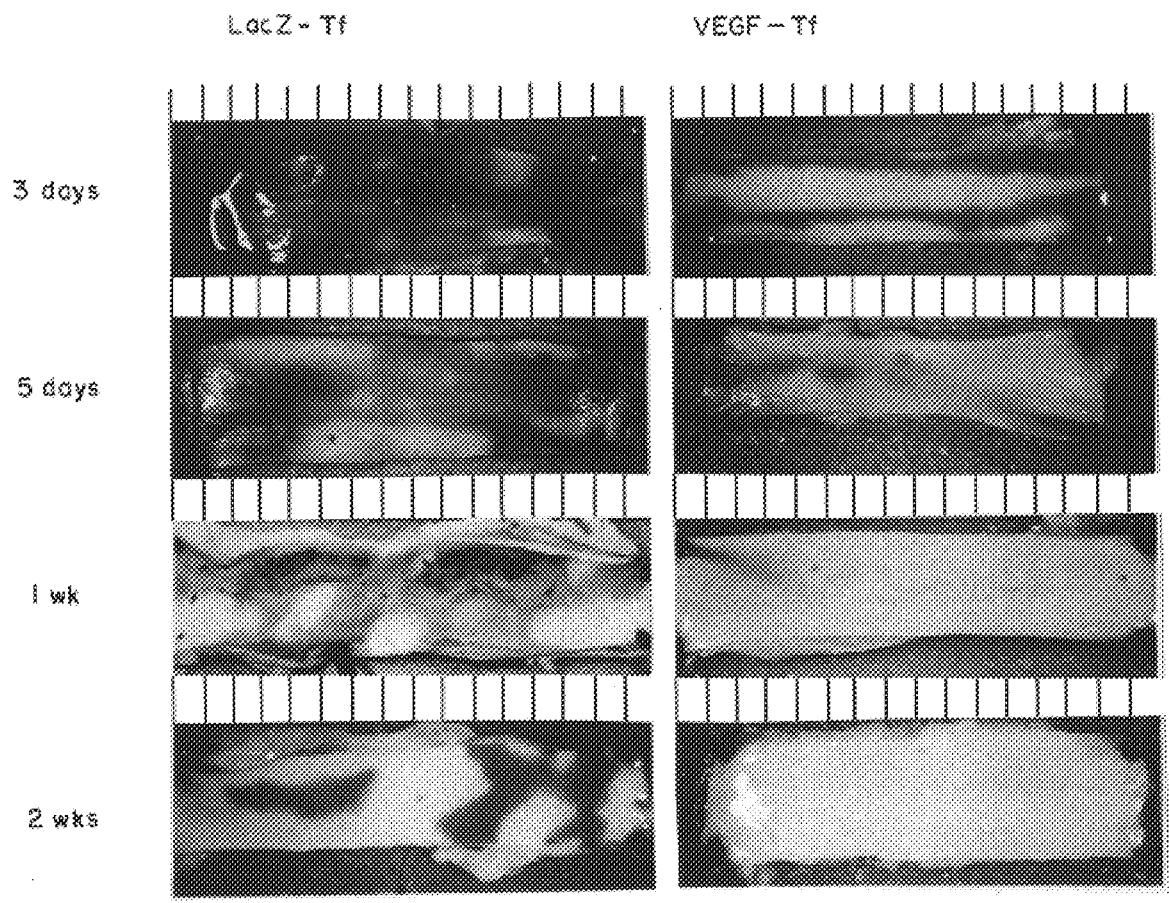
FIGS. 4A and 4B illustrate representative macroscopic appearance of (4A) balloon injured, transfected arteries. (LacZ-Tf and VEGF-Tf) and (4B) contralateral balloon injured, non-transfected arteries (LacZ-nTf and VEGF-nTf) at 3 days, 5 days, 1 wk and 2 wks post-transfection. Re-endothelialized area, not stained by Evans blue dye, appears white.
Figure 4B:
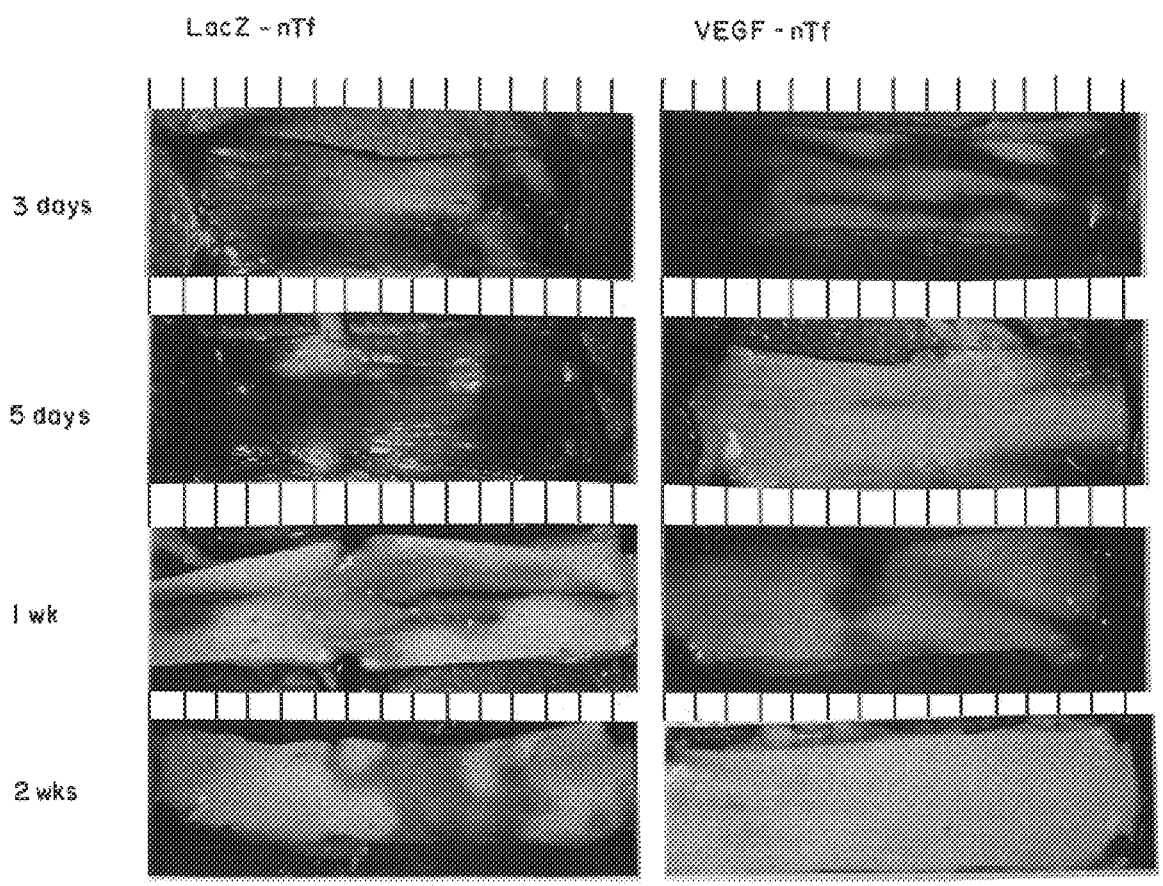
Figures 5A, 5B:
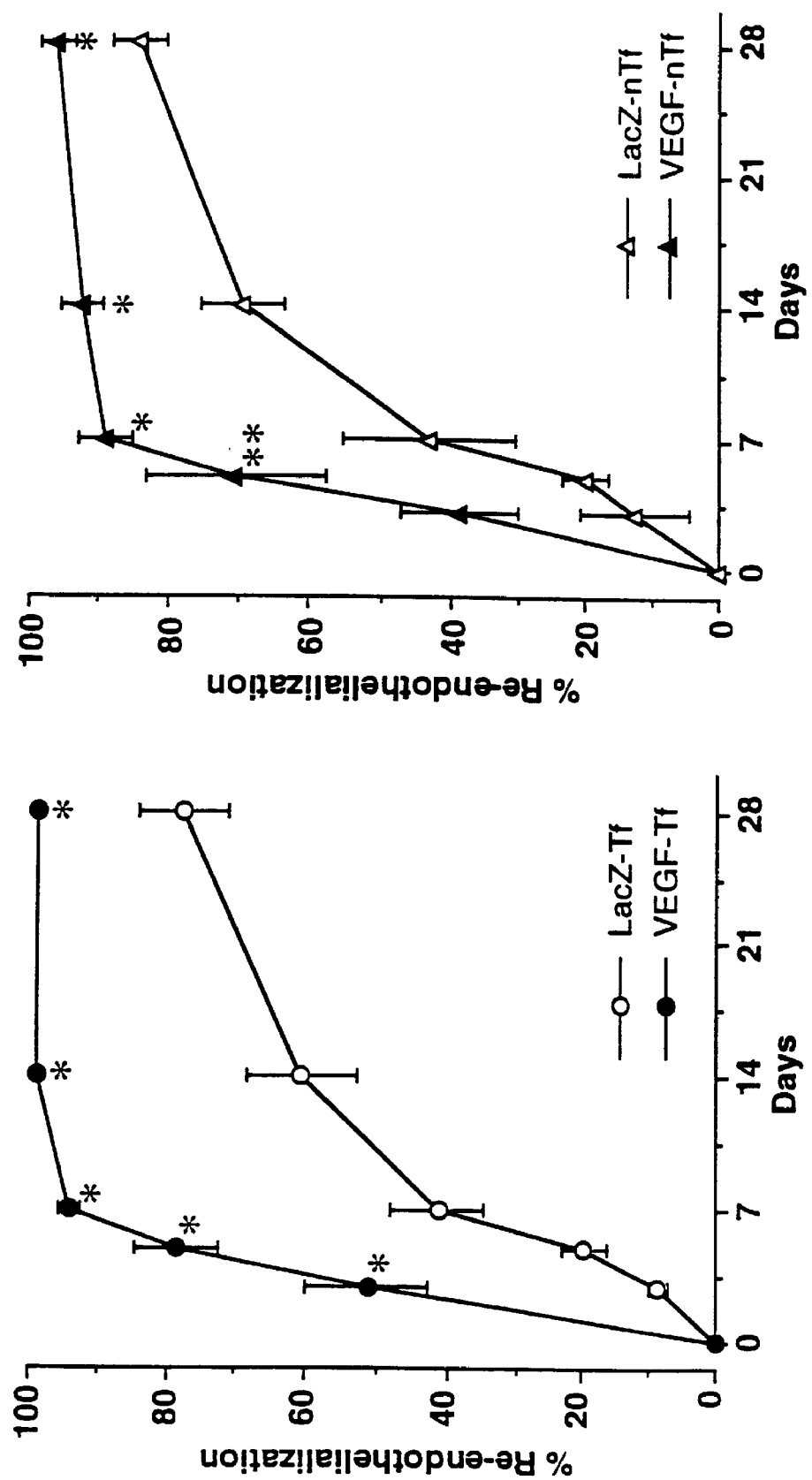
FIGS. 5A and 5B are graphs showing re-endothelialization of injured transfected arteries (5A), and injured non-transfected arteries (5B). (*=p<0.01, **=p<0.05 vs LacZ-Tf or -nTF.)

Planimetric analysis performed with Evans blue dye staining disclosed near-complete rET of the 20-mm long segment of balloon-injured rabbit femoral artery by 7 days among VEGF-transfected arteries, while the extent of rET in LacZ-transfecterd arteries was <50% complete at 7 days and remained nearly 20% incomplete at 4 wks (FIG. 4A, 4C). In 10 VEGF-Tf arteries, rET at 4 wks was in fact 100% complete, a finding which was observed in none of the LacZ-Tf arteries. Re-endothelialization was accelerated not only in arteries trasfected with $phVEGF_{165}$ (VEGF-Tf), but also in the contralateral balloon-injured, non-trasfected arteries (VEGF-nTf) (FIG. 4B, 4C).

Vasomotor reactivity

Figure 6A:
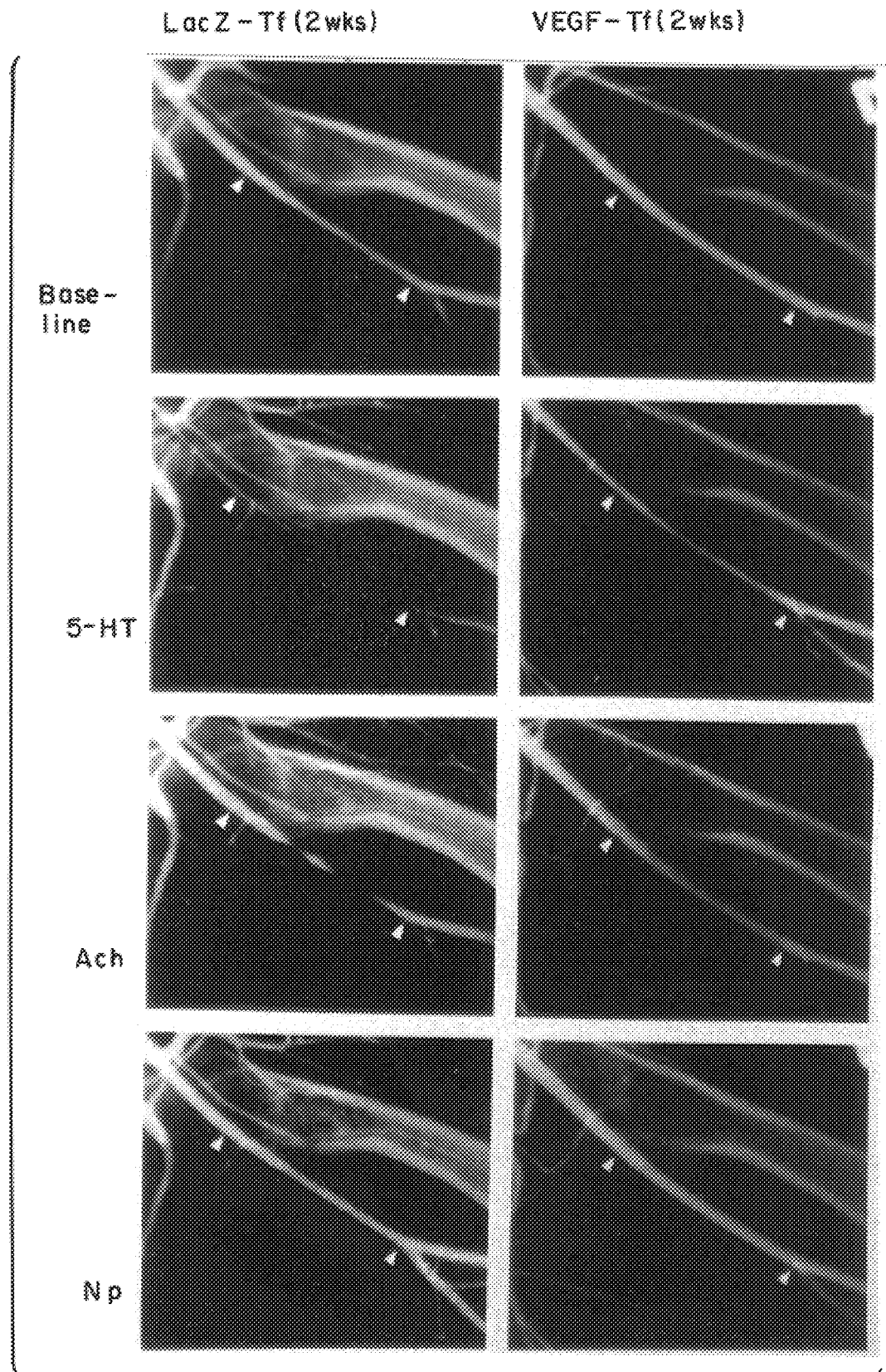
FIGS. 6A and 6B are representative angiograms recorded pre-drug (baseline), and immediately following serotonin creatine sulfate (5-HT), acetylcholine chloride (Ach) and sodium nitroprusside (NP) for LacZ-Tf and VEGF-Tf arteries at 2 wks post-transfection (6A). The arterial segment between the two arrow-heads in each angiogram indicates the site of balloon-injury.
Figure 6B:
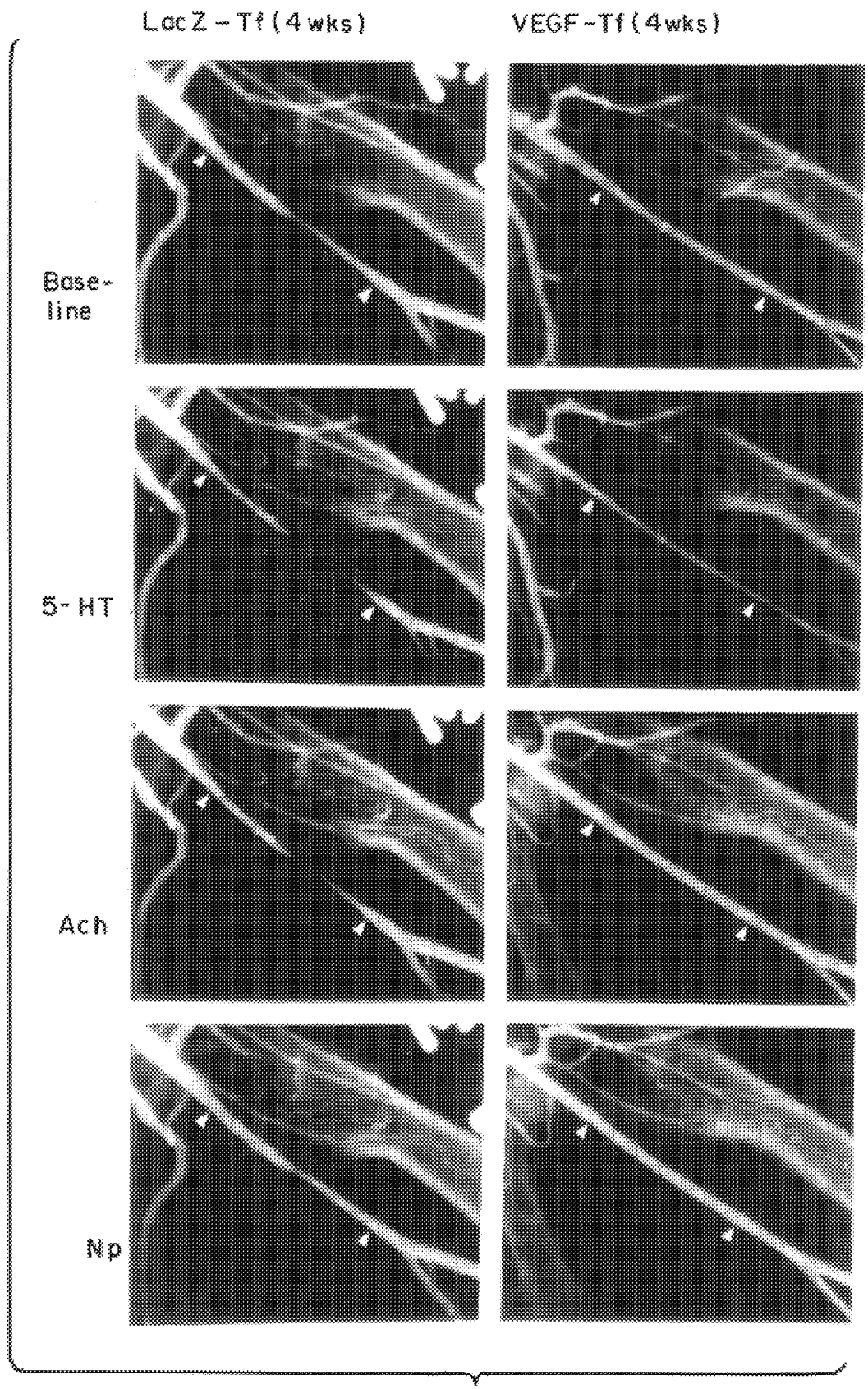
Figure 7:
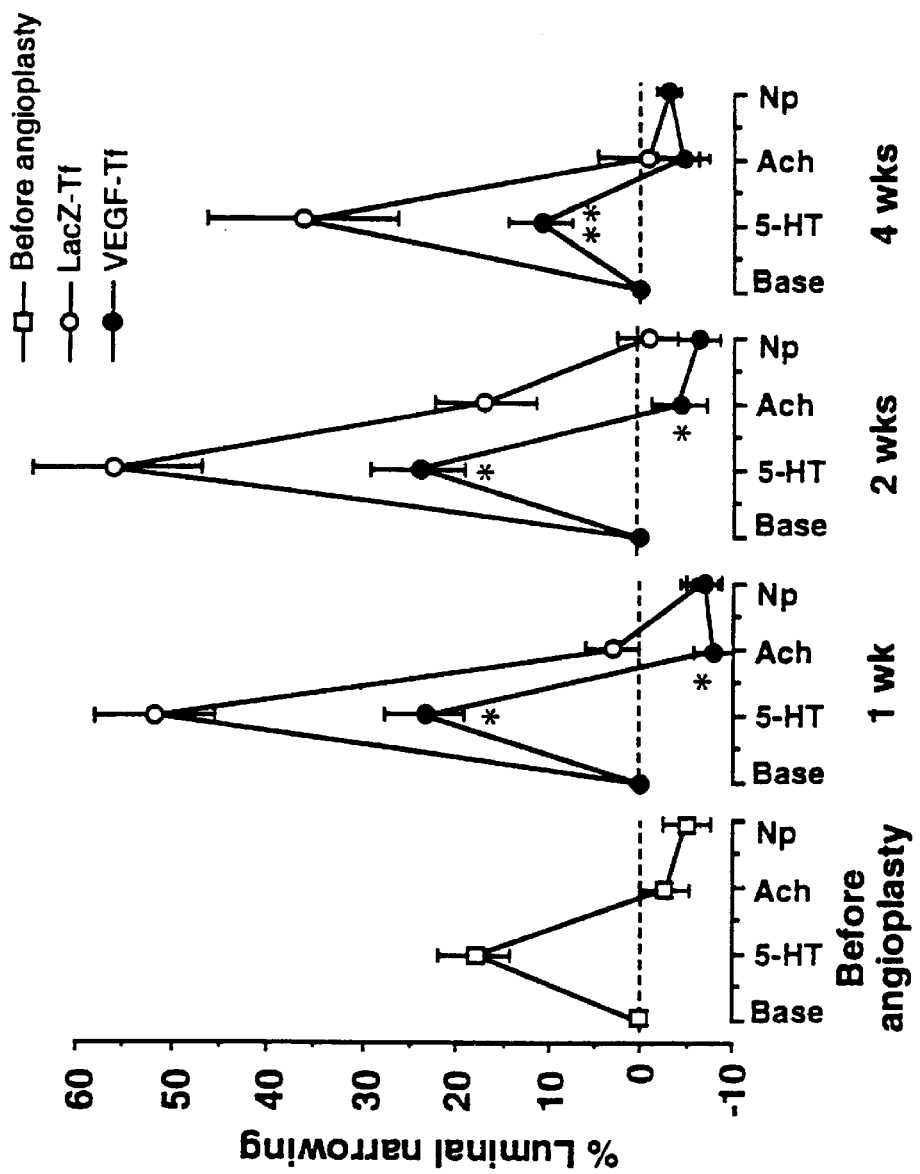
FIG. 7 is a quantitative angiographic analysis of vasomotor response at 1 wk, 2 wks and 4 wks post-transfection. 5-HT produced mild vasoconstriction in normal (non-balloon injured) rabbit femoral artery and severe constriction in LacZ-tf, especially at 1 and 2 wks after injury. Significantly less vasoconstriction was seen in VEGF-Tf, and was in fact similar to or less than that observed in normal (i.e. non-injured, non-transfected) arteries. Ach infusion caused slight dilatation in non-balloon injured arteries. Post-balloon injury, Ach failed to dilate LacZ-Tf at 1 and 2 wks, whereas Ach induced dilatation in VEGF-Tf. Again, vasomotor response in VEGF-Tf was similar to that observed in normal non-injured arteries. Np produced mild dilatation before injury, and equivalent dilation in both LacZ-Tf and VEGF-Tf (*=p<0.01, **=p<0.05 vs LacZ-Tf).

Previous investigations of rET have demonstrated that restoration of anatomic integrity and recovery of physiologic function do not proceed simultaneously (Tanaka, et al., Circulation, 33:1788–1803 (1993), Shimokawa, et al., Circ. Res., 61:256–270 (1987), and Weidinger, et al., Circulation, 81:1667–1679 (1990)). Accordingly, we determined the vasomotor response to endothelium-dependent agonists using quantitative angiography. Consistent with the previous experience of Weidinger, et al. (supra), control rabbits transfected with LacZ demonstrated persistent impairment in vasomotor response to endothelium-dependent agents at 4 wks post-injury (Table 1). In contrast, arteries trasfected with $phVEGF_{165}$ disclosed recovery of near-normal endothelium-dependent vasoreactivity within 1 wk (FIGS. 6 and 7). A similar benefit was observed for the contralateral, balloon-injured, non-transfected limb (Table 1).

TABLE 1

Vasoconstriction (+) or vasodilation (−) in response to endothelium-dependent and -independent agonsits following $phVEGF_{165}$ gene therapy

| | 1 wk | | | 2 wks | | | 4 wks | | |
|---|---|---|---|---|---|---|---|---|---|
| | 5-HT | Ach | Np | 5-HT | Ach | Np | 5-HT | Ach | Np |
| LacZ-Tf | (+) 48.6 ± 5.4 | (+) 4.2 ± 2.8 | (−) 4.8 ± 2.3 | (+) 56.3 ± 8.0 | (+) 15.1 ± 4.8 | (−) 0.9 ± 2.9 | (+) 35.5 ± 9.1 | (−) 1.1 ± 5.1 | (−) 6.0 ± 4.5 |
| VEGF-Tf | (+) 24.2 ± 4.1* | (−) 6.8 ± 2.2* | (−) 6.6 ± 1.7 | (+) 24.2 ± 4.5* | (−) 3.3 ± 2.8* | (−) 5.4 ± 2.2 | (+) 10.6 ± 2.3† | (−) 4.6 ± 2.9 | (−) 3.1 ± 1.3 |
| LacZ-nTf | (+) 53.6 ± 5.0 | (+) 12.8 ± 6.6 | (−) 5.8 ± 3.8 | (+) 48.4 ± 5.6 | (+) 10.8 ± 5.0 | (+) 0.7 ± 2.0 | (+) 29.0 ± 4.2 | (−) 4.6 ± 2.7 | (−) 6.5 ± 3.1 |
| VEGF-nTF | (+) 29.3 ± 3.4* | (−) 0.5 ± 3.0† | (−) 8.0 ± 2.2 | (+) 28.3 ± 2.6* | (−) 1.3 ± 1.1† | (−) 2.1 ± 1.4 | (+) 13.6 ± 3.1† | (−) 2.7 ± 2.5 | (−) 6.6 ± 4.7 |

Figure 8A:
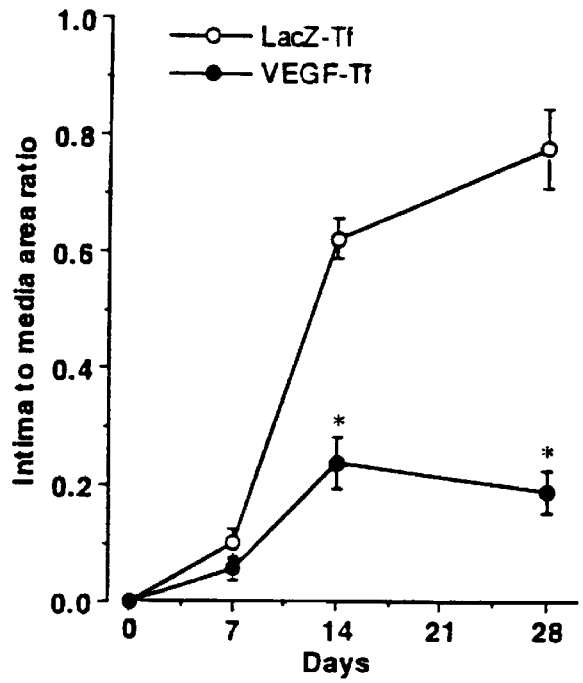
FIGS. 8A and 8B are graphs illustrating that LacZ-Tf arteries showed progressive neointimal thickening through 4 wks. Significantly less intimal thickening was observed among VEGF-Tf arteries, including regression of intimal thickening between 2 to 4 weeks (*=p<0.01, vs LacZ-Tf). (8A) Contralateral balloon-injured, non-transfected artery in VEGF group (VEGF-nTf) developed less intimal thickening and displayed no progression during wks 2 to 4, compared to LacZ-nTf (*=p<0.01, **=p<0.05 vs LacZ-nTf)(FIG. 8B).
Figure 8B:
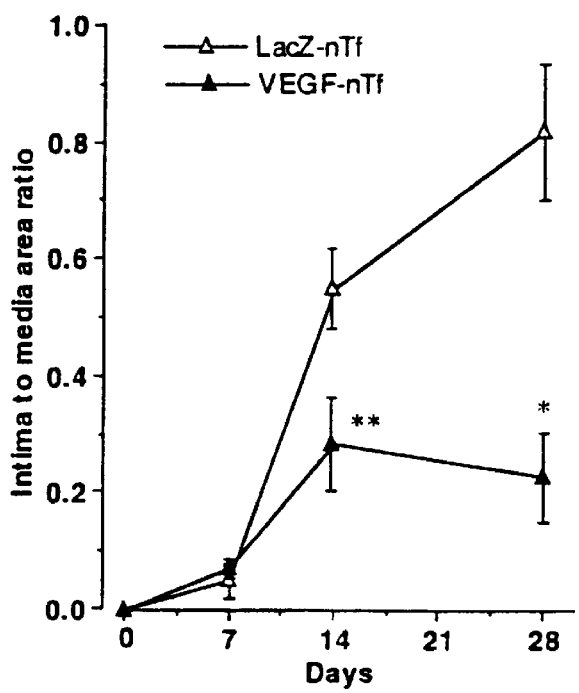
Figure 9:
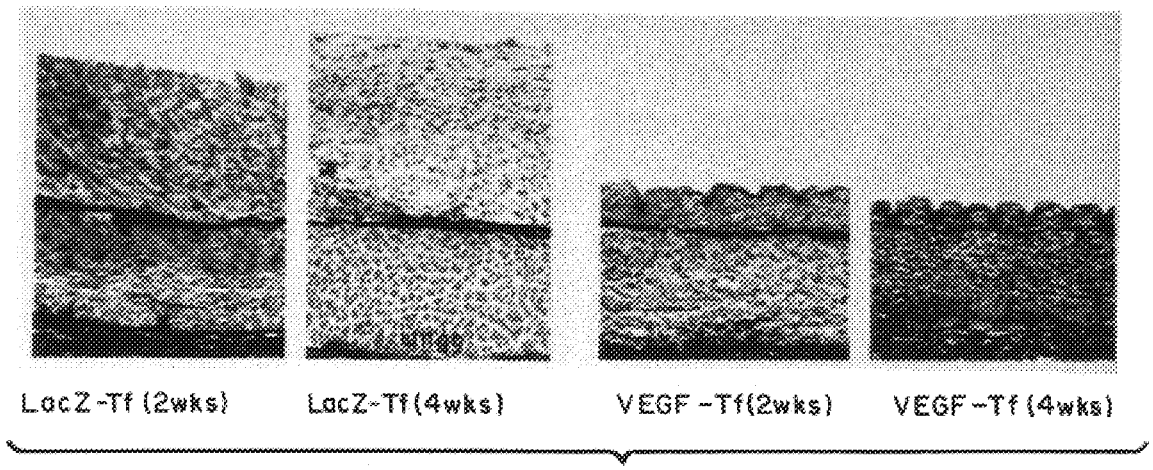
FIG. 9 shows representative effect of transfection on intimal thickening for LacZ-Tf and VEGF-Tf at 2 wks and 4 wks post-transfection.

Values represent change in percent luminal narrowing;
*= $p < 0.01$ vs control,
†= $p < 0.05$ vs control Neointimal thickening The impact of accelerated of rET on neointimal thickening was evaluated by light microscopic examination as the ratio of intimal area to medial area (I/M ratio) in longitudinally cut sections (FIG. 8). LacZ-Tf arteries showed progressive neointimal thickening through 4 wks (1 wk=I/M= 0.11±0.02; 2 wks=0.59±0.04; 4 wks=0.69±0.10). In contrast, VEGF-Tf arteries disclosed significantly less intimal thickening, including regression of intimal thickening between wks 2 and 4 (1 wk=0.06±0.02; 2 wks=0.20±0.05, p<0.1; 4 wks=0.14±0.02, p<0.01).

Moreover, the I/M ratio of the contralateral balloon-injured artery in the VEGF gene transfer group (VEGF-nTf) developed less intimal thickening and displayed no progression during 2 to 4 wks, compared t;o the contralateral artery of the LacZ controls (LacZ-nTf, 1 wk=0.05±0.03; 2 wks= 0.54±0.06; 4 wks=084±0.09; VEGF-nTf, 1 wk=0.09±0.02; 2 wks=0.29±0.08, p<0.05; 4 wks=0.31±0.09, p<0.01.

Proliferative activity

Figure 10:
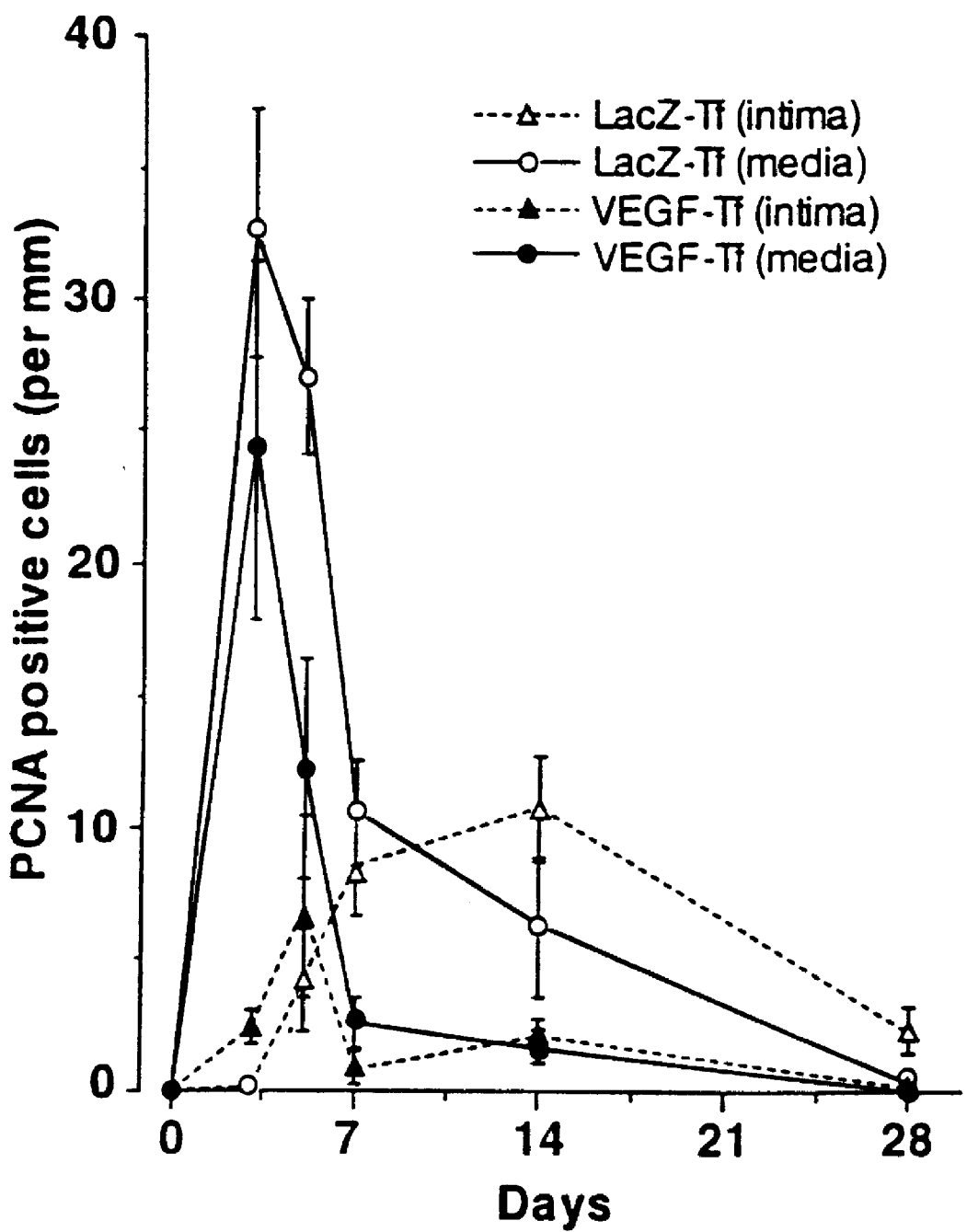
FIG. 10 is a graph showing proliferative activity in media of both LacZ-Tf (open circle) and VEGF-Tf (closed circle) peaked at 3d post-injury; over remaining 4 wks, proliferative activity decreased more rapidly in VEGF-Tf than in LacZ-Tf. In intima, time course of proliferation was more protracted for LacZ-Rf (open triangle) than VEGF-Tf (closed triangle).

The reduction in neointimal thickening observed with ph $VEGF_{165}$-accelerated rET was associated with a concomitant reduction in proliferative activity in both the media and neoimtimal (FIG. 10). Cellular proliferation in the media of LacZ-Tf reached a peak at 3 days post-injury and then decreased gradually over the remaining 4 wks (3d=32.5±4.7 PCNA-positive cells/mm; 5d=27.1±2.9; 1 wk=10.5±2.0; 2 wks=6.2±2.7; 4 wks=0.3±0.2). Proliferative activity in the medium of VEGF-Tf also peaked at 3 days post-gene transfer (24.7±6.8 cells/mm), but then decreased rapidly (5d=12.2±4.2 cells/mm; 1 wk=2.6±1.0; 2 wks=1.6±0.5; 4 wks=0.1±0.0). Selective immunostaining of adjacent sections established that proliferating cells were predominantly smooth muscle cells.

Temporal differences in proliferative activity were also observed for the neointimal of LacZ vs VEGF transfected animals. Neointimal proliferation in LacZ-Tf arteries continued to crescendo up to 2 wks post-trasfection (3d=0.2±0.1 cells/mm; 5d=4.1±1.9; 1 wk=8.6±2.0; 2 wks=10.7±2.0; 4 wks=2.3. For VEGF-Tf, neointimal proliferative activity peaked at 5 days and then fell precipitously (3d=2.4±0.6 cells/mm; 5d=7.0±3.4; 1 wk=0.8±0.3; 2 wks=2.0±0.7; 4 wks=0.1±0.1).

Figure 11:
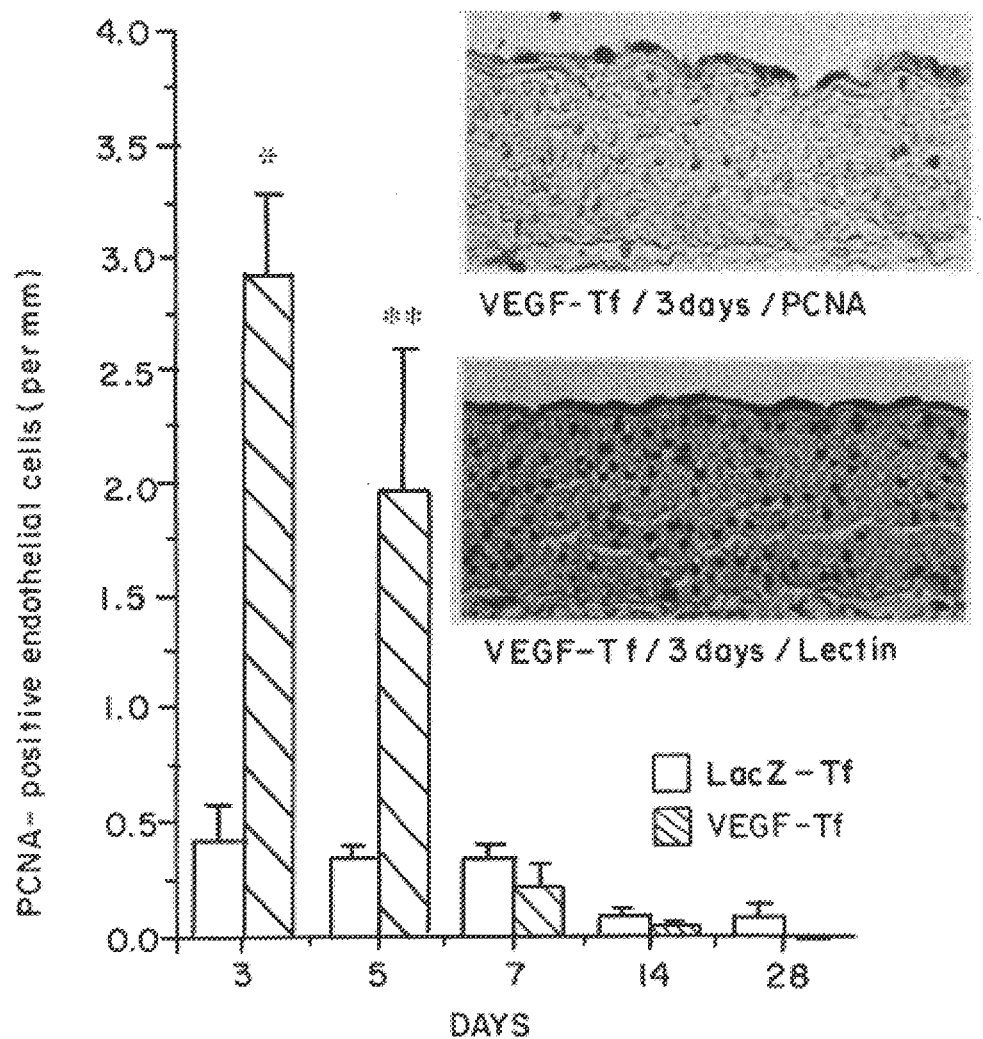
FIG. 11 shows EC proliferation in VEGF-Tf exceeded that of LacZ-Tf at 3d and 5d. Upper photomicrograph shows PCNA-positive cells on luminal side of internal elastic membrane, 3d post-gene transfer; BSI-lectin in lower photomicrograph identifies these as ECs. (*=p<0.01; **=p<0.05).

PCNA-positive cells were identified as ECs by positive BSI lectin staining of apparently identical cells located along the luminal border of adjacent (serially cut) histologic sections. Proliferative activity of ECs was constant throughout the 4 wks following balloon injury in LacA-Tf. In contrast, EC proliferation in VEGF-Tf arteries demonstrated a prominent peak at 3d, and was then reduced by 1 wk post-transfection (FIG. 11).

Thromboresistance

Thromboresistance constitutes an important consideration in the immediate post-angioplasty setting. This is particularly true when angioplasty is performed for acute myocardial infarction, in which case the risk of subacute reocclusion is increased. In the current study, ph $VEGF_{165}$-accelerated rET led to augmented thromboresistance. Specifically, thrombotic occlusion developed less frequently in animals transfected with ph $VEGF_{165}$ (2/64) than in those transfected with Lac-Z(14/64) (p<0.001).

Gene expression

VEGF gene expression assessed by RT-PCR in 3 normal, non-instrumented rabbits, and rabbits transfected with ph $VEGF_{165}$ at 0 day (pre-angioplasty), 3d, 5d, 1 wk, 2 wks and 4 wks (n=3 each). Gene expression was observed as early as 3d, persisted through 2 wks, and diminished by 3 wks (FIG. 12).

RT-PCR was also performed on sections from other organs and disclosed no mRNA expression of VEGF at any sit remote from the VEGF-transfected arterial segment (FIG. 12).

Four rabbits were transfected with LacZ and sacrificed 5d later; quantitative examination comprising all cells in selected light microscopic fields indicated that transfection efficiently was <0.1%, consistent with previous reports (Isner, et al., supra and Mancini, et al., supra).

Previous investigations of rET in a variety of animal models have demonstrated that restoration of anatomic integrity and recovery of physiologic function do not proceed simultaneously (Tanaka, et al., supra, Shimokawa, et al., supra, and Weidinger, et al., supra). Accordingly, we attempted to characterize the functional behavior of VEGF-induced re-endothelialization in three ways. First, we determined the vasomotor response to endothelium-dependent agonists. Consistent with the previous experience of Weidinger, et al. (supra), control rabbits transfected with LacZ demonstrated persistent impairment in response to Ach and 5-HT at four weeks post-injury. In contrast, arteries transfected with $phVEGF_{165}$ disclosed recovery of near-normal endothelium-dependent response within one week. Parenthetically, the physiologic response among VEGF-Tf rabbits at four weeks can be assumed to represent the response of restored endothelium in the absence of ongoing $VEGF_{165}$ secretion, since analyses using RT-PCR in the present and previous (Isner, et al., supra) studies have consistently disclosed no evidence of transgene expression beyond 3 weeks.

The reduced proliferative activity among smooth muscle cells, and associated reduction in intimal thickening observed in arterial segments subjacent to sites of VEGF gene transfer constitute a second index of expeditiously restored EC function. The precise mechanism by which the neo-endothelium modulates intimal hyperplasia remains to be clarified (vide infra), but presumably reflects prompt restoration of anti-proliferative features characteristic of healthy ECs.

VEGF-induced rET appeared to result in improved thromboresistance, a function of particular importance in the post-angioplasty setting. In fact, given the current trend favoring increased application of angioplasty in the treatment of acute myocardial infarction, VEGF gene transfer for the purpose of stabilizing acutely ruptured plaque may have additional merit.

EXAMPLE 2

Rendothelilization of an Arterial Segment After Balloon Deendothelialization and Stent Implantation Plasmids The pGSVLacZ vector is described above.

The cDNA to be used in this example encodes the 165 amino acid isoform of VEGF and has been described previously. The plasmid into which the VEGF cDNA has been inserted, $phVEGF_{165}SR$, is a simple eucaryotic expression plasmid that utilizes cytomegalovirus (CMV) promoter/enhancer to drive VEGF expression. This plasmid is a derivative of pCG (Tanaka, et al., Cell, 60:375–386 (1990)). The backbone plasmid vector is derived from pBSM13+. A cassette encoding the kanamycin resistance gene has been inserted, and the SV40 origin of replication present in the original vector ($phVEGF_{165}$) has been largely removed. The CMV promoter is from positions −522 to +72 relative to the CMV cap site. Upstream from the phVEGF$_{165}$SR coding sequence is the HSV thymidine kinase gene 5' leader from positions +51 to +114 relative to the thymidine kinase cap site. Downstream from the VEGF coding sequence is the rabbit b-globin gene sequence from positions +905 to +2080 relative to the b-globin cap site.

To confirm plasmid identity, the entire phVEGF,$_{165}$SR sequence (6609 bp) has been determined using 30 sequence primers. The structure of the double-stranded DNA was determined by the cycle sequencing method using fluorescent dideoxy terminator nucleotides with an Applied Biosystem 373A Automated sequencer. Sequences were analyzed on Macintosh Quadra computers with MacVector and Sequence Navigator software. The quality control for this sequencing analysis consists of parallel sequence analyses of Bluescript and M13 controls. This analysis revealed a 99.1% sequence homology between our determined sequence and the predicted sequence of the 6609 bp plasmid.

Sequence of the VEGF coding region was determined on both strands and it was in 100% agreement with the predicted sequence.

METHODS

Procedures were performed using New Zealand rabbits (3.5–4.0 kg). All animals received aspirin (100 mg/day) for 1 week before the procedure and the treatment was continued until sacrifice. All received heparin (1000 units) and antibiotics (2.5 mg/kg) at the time of the procedure. The protocol was designed to distinguish both the local and the systemic effect of the therapy.

A) Group A: VEGF treated group
1) Side One-VEGF treated:
   Fogarty balloon deendothelialization of external iliac artery.
   Stent (Johnson and Johnson PS 204C) implantation in external iliac artery using a 3.0 mm PTCA balloon at 8 Atm inflation pressure.
   Local application of 800 μg of ph VEGF$_{165}$ SR plasmid DNA using a 3.5 mm diameter Hydrogel coated PTCA balloon at 6 Atm.
2) Side Two-no treatment
   Fogarty balloon deendothelialization of external iliac artery.
   Stent (Johnson and Johnson PS 204C) implantation in external iliac artery using a 3.0 mm PTCA balloon at 8 Atm inflation pressure.

B) Group B: β-galactosidase treated group
1) Side One-β-galactosidase treated:
   Fogarty balloon deendothelialization of external iliac artery.
   Stent (Johnson and Johnson PS 204C) implantation in external iliac artery using a 3.0 mm PTCA balloon at 8 Atm inflation pressure.
   Local application of 800 μg of the plasmid pGSVLacZ containing a nuclear target β-galactosidase sequence using a 3.5 mm diameter Hydrogel coated PTCA balloon at 6 Atm.
2) Side Two-no treatment:
   Fogarty balloon deendothelialization of external iliac artery.
   Stent (Johnson and Johnson PS 204C) implantation in external iliac artery using a 3.0 mm PTCA balloon at 8 Atm inflation pressure.

All animals were sacrificed 7 days after stent implantation. The percentage of endothelial covering of the stent surface was evaluated by light microscopy and by scanning electron microscopy.

Results:
Group A=6 rabbits.
Group B=4 rabbits.
Percent reendothelialization:
Group A (VEGF) treated side=87.0±5.0
control side=42.2±11.3
Group B (β-galactosidase) treated side=2.1±1.1
control side=21.6±14.8

The treated side of the VEGF group had significantly better endothelial coverage at day 7 than all the other sides (p<005).

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

---

What is claimed is:

1. A method for inducing reendothelialization in an injured blood vessel in a human host, wherein said injured blood vessel comprises a denuded portion of its endothelial lining, comprising:
   (a) selecting a human host having an injured blood vessel comprising a denuded portion of its endothelial lining;
   (b) administering to cells of said injured blood vessel in the human host an effective amount of DNA that encodes vascular endothelial growth factor (VEGF) admixed with an hydrogel polymer; and
   (c) expressing the VEGF encoded by said DNA in said cells such that reendothelialization occurs in said denuded portion of said injured blood vessel.

2. The method of claim 1, wherein said blood vessel injury is the result of balloon angioplasty.

3. The method of claim 1, wherein said blood vessel injury is the result of deployment of an endovascular stent.

4. The method of claim 1, further comprising performing balloon angioplasty and wherein said DNA encoding VEGF is administered to said injured blood vessel at the same time as said angioplasty.

5. A method of reducing restenosis in a human host, comprising:
   (a) selecting a human host at risk for restenosis resulting from deployment of an endovascular stent in a blood vessel, wherein said deployment results in denuding of a portion of the endothelial lining of said blood vessel;
   (b) administering to cells of said blood vessel in the human host an effective amount of DNA that encodes vascular endothelial growth factor (VEGF) admixed with an hydrogel polymer; and
   (c) expressing the VEGF encoded by said DNA in said cells such that restenosis in said denuded portion of said blood vessel is reduced.

\* \* \* \* \*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

GAGGGCAGAA TCATCACGAA GT 22

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:2:

TCCTATGTGC TGGCCTTGGT GA 22